US 6,696,487 B2

(12) United States Patent
Gerusz et al.

(10) Patent No.: US 6,696,487 B2
(45) Date of Patent: Feb. 24, 2004

(54) FUNGICIDAL PHENYL(THIO)UREA AND PHENYL(THIO)CARBAMATE DERIVATIVES

(75) Inventors: Vincent Gerusz, Lyons (FR); Darren James Mansfield, Lyons (FR); José Perez, Lyons (FR); David Tickle, Essex (GB); Jean-Pierre Vors, Lyons (FR); Derek Baldwin, Essex (GB); Thomas Lawley Hough, Cambridge (GB); Dale Robert Mitchell, Essex (GB)

(73) Assignee: Bayer Cropscience S.A. (FR)

( * ) Notice: Subject to any disclaimer, the term of this patent is extended or adjusted under 35 U.S.C. 154(b) by 0 days.

(21) Appl. No.: 09/923,124

(22) Filed: Aug. 6, 2001

(65) Prior Publication Data

US 2003/0008884 A1 Jan. 9, 2003

(30) Foreign Application Priority Data

Aug. 4, 2000 (FR) .............................................. 00 10305

(51) Int. Cl.[7] ........................ A01N 47/10; A01N 47/28; C07C 271/40; C07C 275/28
(52) U.S. Cl. ...................... 514/476; 514/478; 514/586; 514/587; 514/596; 514/598; 558/234; 558/236; 560/24; 560/27; 560/29; 562/27; 562/443; 562/444; 564/28; 564/48; 564/52
(58) Field of Search ................ 558/234, 236; 560/24, 27, 29; 562/443, 444, 27; 564/28, 48, 52; 514/476, 478, 586, 587, 596, 598

(56) References Cited

U.S. PATENT DOCUMENTS

| 4,005,223 A | 1/1977 | Sirrenberg et al. ......... 424/322 |
| 4,328,248 A | 5/1982 | Boger et al. ................ 424/326 |
| 4,540,578 A | 9/1985 | Chou et al. ................. 514/349 |
| 4,914,098 A | 4/1990 | Boger et al. ................ 514/274 |
| 5,066,667 A | 11/1991 | Ehrenfreund et al. ....... 514/381 |
| 6,083,970 A | 7/2000 | Muller et al. ............... 514/407 |

FOREIGN PATENT DOCUMENTS

DE 3102590 A1 8/1982

Primary Examiner—Richard L. Raymond
(74) Attorney, Agent, or Firm—Ostrolenk, Faber, Gerb & Soffen, LLP

(57) ABSTRACT

The invention relates to compounds of formula (I), and also to salts thereof, which have fungicidal activities:

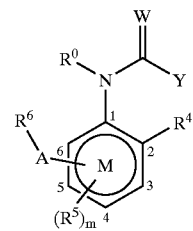

(I)

in which the various radicals and substituents are as defined in the description, and also to the fungicidal compositions containing them and to methods for combating the phytopathogenic fungi of crops using these compounds and compositions.

19 Claims, No Drawings

FUNGICIDAL PHENYL(THIO)UREA AND PHENYL(THIO)CARBAMATE DERIVATIVES

The present invention relates to novel fungicidal phenyl (thio)urea and phenyl(thio)carbamate derivatives, to a process for preparing them and to fungicidal compositions containing them.

Patent application WO 95/22532 describes phenyltriazolinones with herbicidal activity. In particular, the compound of formula (A) is presented, for which no characteristics are given:

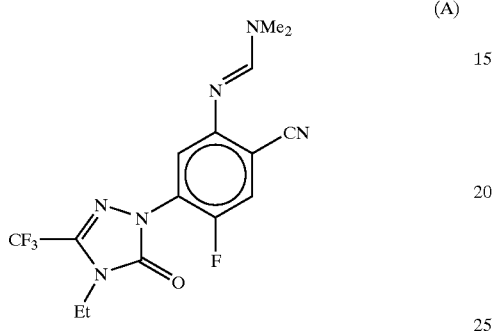

(A)

The abstract and the composition claims and use claims of the said patent application refer solely to the use of such compounds for herbicidal purposes; specifically, the description supports this description solely with herbicidal activity data. Mention is simply made in the said patent application of a possible fungicidal activity for certain compounds. However, no fungicidal activity data is produced. There are no indications regarding the nature of the compounds liable to have such fungicidal activity, and there is no disclosure as regards the fungicidal activity of compound (A).

The Applicant has now discovered that certain novel carbamates, thiocarbamates, ureas and thioureas, and also derivatives thereof, have fungicidal activity. Thus, the invention relates to the compounds of general formula (I) and also to salts thereof:

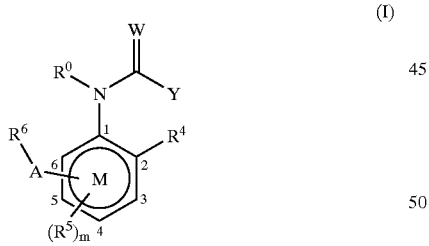

(I)

in which
W represents O or S;
Y represents a radical —NR$^1$R$^2$, —OR$^3$ or —SR$^3$;
R$^0$ represents an alkyl, alkenyl, alkynyl, acyl, cyano, carbocyclyl or heterocyclyl radical, each of which may be substituted; or a hydrogen atom; or represents a single bond with Y;
R$^1$ and R$^2$, which may be identical or different, represent any one of the groups defined for R$^0$; or —NR$^a$R$^b$, —OR$^a$, —SR$^a$, —S(O)R$^a$ or —S(O)$_2$R$^a$, in which R$^a$ and R$^b$, which may be identical or different, represent an alkyl, alkenyl, alkynyl, acyl, cyano, sulphonyl, carbocyclyl or heterocyclyl radical, each of which may be substituted; or a hydrogen atom;

R$^3$ represents any one of the groups defined for R$^0$;
R$^1$ and R$^2$ or R$^1$ and R$^0$ or R$^3$ and R$^0$ or R$^a$ and R$^b$, taken together with the atoms connecting them, may form an optionally substituted ring, the assembly thus forming a carbocyclyl or heterocyclyl group;
R$^4$ represents an alkyl, alkenyl, alkynyl, carbocyclyl or heterocyclyl radical, each of which may be substituted; hydroxyl; mercapto; azido; nitro; a halogen atom; cyano; acyl; optionally substituted amino; cyanato, thiocyanato; —SF$_5$; —OR$^a$; —SR$^a$ or —Si(R$^a$)$_3$, in which R$^a$ is as defined above;
m is an integer chosen from 0, 1, 2 and 3;
R$^5$, when it is present, is identical to or different from any one of the other radicals R$^5$, and represents any one of the groups defined for R$^4$;
R$^6$ represents an optionally substituted carbocyclyl or heterocyclyl radical; and
A represents a direct bond, —O—, —S(O)$_n$—, —NR$^9$—, —CR$^7$=CR$^7$—, —C≡C—, —A$^1$—, —A$^1$—A$^1$—, —O—(A$^1$)$_k$—O—, —O—(A$^1$)$_k$—, —A$^3$—, —A$^4$—, —A$^1$O—, —A$^1$S(O)$_n$—, —A$^2$—, —OA$^2$—, —NR$^9$A$^2$—, —OA$^2$—A$^1$—, —OA$^2$—C(R$^7$)=C(R$^8$)—, —S(O)$_n$A$^1$—, —A$^1$—A$^4$—, —A$^1$—A$^4$—C(R$^8$)=N—N=CR$^8$—, —A$^1$—A$^4$—C(R$^8$)=N—X$^2$—X$^3$—, —A$^1$—A$^4$—A$^3$—, —A$^1$—A$^4$—N(R$^9$)—, —A$^1$—A$^4$—X—CH$_2$—, —A$^1$—A$^4$—A$^1$—, —A$^1$—A$^4$—CH$_2$X—, —A$^1$—A$^4$—C(R$^8$)=N—X$^2$—X$^3$—X$^1$—, —A$^1$—X—C(R$^8$)=N—, —A$^1$—X—C(R$^8$)=N—N=CR$^8$—, —A$^1$—X—C(R$^8$)=N—N(R$^9$)—, —A$^1$—X—A$^2$—X$^1$—, —A$^1$—O—A$^3$—, —A$^1$—O—C(R$^7$)=C(R$^8$)—, —A$^1$—O—N(R$^9$)—A$^2$—N(R$^9$)—, —A$^1$—O—N(R$^9$)—A$^2$—, —A$^1$—N(R$^9$)—A$^2$—N(R$^9$)—, —A$^1$—N(R$^9$)—A$^2$—, —A$^1$—N(R$^9$)—N=C(R$^8$)—, —A$^3$—A$^1$—, —A$^4$—A$^3$—, —A$^2$—NR$^9$—, —A$^1$—A$^2$—X$^1$—, —A$^1$—A$^1$—A$^2$—X$^1$—, —O—A$^2$—N(R$^9$)—A$^2$—, —CR$^7$=CR$^7$—A$^2$—X$^1$—, —C≡C—A$^2$—X$^1$, —N=C(R$^8$)—A$^2$—X$^1$—, —C(R$^8$)=N—N=C(R$^8$)—, —C(R$^8$)=N—N(R$^9$)—, —(CH$_2$)$_2$—O—N=C(R$^8$)— or —X—A$^2$—N(R$^9$)—
in which
n represents 0, 1 or 2,
k represents 1 to 9,
A$^1$ represents —CHR$^7$—,
A$^2$ represents —C(=X)—,
A$^3$ represents —C(R$^8$)=N—O—,
A$^4$ represents —O—N=C(R$^8$)—,
X represents O or S,
X$^1$ represents O, S, NR$^9$ or a direct bond,
X$^2$ represents O, NR$^9$ or a direct bond,
X$^3$ represents a hydrogen atom, —C(=O)—, —SO$_2$— or a direct bond,
R$^7$, which may be identical to or different from any one of the other radicals R$^7$, represents an alkyl, alkenyl, alkynyl, cyano, acyl, hydroxyl, alkoxy, haloalkoxy, alkylthio, cycloalkyl or phenyl radical, each of which may be substituted; or represents a hydrogen atom or a halogen atom;
R$^8$, which may be identical to or different from any one of the other radicals R$^8$, represents an alkyl, alkenyl, alkynyl, alkoxy, alkylthio, carbocyclyl or heterocyclyl radical, each of which may be substituted; or represents a hydrogen atom;
R$^9$, which may be identical to or different from any one of the other radicals R$^9$, represents an optionally substituted alkyl radical, an optionally substituted carbocyclyl or heterocyclyl radical, a hydrogen atom or an acyl radical; or two groups $R^9$ in A, taken together with the atoms connecting them, form a 5- to 7-membered ring;

the straight part of the divalent radicals —A— is linked to $R^6$;

—A—$R^6$ and $R^5$, taken together with the benzene nucleus M, can form an optionally substituted fused cyclic system.

According to one preferred aspect, the invention relates to the compounds of general formula (I) and the salts thereof, in which:

$R^0$ represents an alkyl, acyl or cyano radical, each of which may be substituted with alkoxy, haloalkoxy, alkylthio, halogen atoms or phenyl optionally substituted with alkyl, haloalkyl, alkoxy, haloalkoxy, alkylthio or halogen atoms; or represents a hydrogen atom;

$R^1$, $R^2$ and $R^3$ are as defined above;

$R^4$ represents an alkyl, alkenyl, alkynyl, alkoxy or alkylthio radical, each of which may be substituted with alkoxy, haloalkoxy, alkylthio, halogen atoms or phenyl optionally substituted with alkyl, haloalkyl, alkoxy, haloalkoxy, alkylthio or halogen atoms; or represents hydroxyl; halogen atoms; cyano; acyl (preferably —C(=O)$R^c$, —C(=S)$R^c$ or —S(O)$_p R^c$, in which p represents 0, 1 or 2 and $R^c$ represents alkyl, haloalkyl, alkoxy, haloalkoxy, alkylthio, amino, monoalkylamino, dialkylamino or phenyl optionally substituted with alkyl, haloalkyl, alkoxy, haloalkoxy or alkylthio; or phenyloxy, phenylthio, carbocyclyl or heterocyclyl);

m represents 0 or 1;

when it is present, $R^5$ represents a group defined for $R^4$ according to this characteristic;

A represents a direct bond, or the divalent radicals —O—, —S—, —NR$^9$—, —CHR$^7$— or —O—CHR$^7$—, in which $R^9$ represents alkyl, alkenyl or alkynyl, each of which may be substituted with alkoxy, haloalkoxy, alkylthio, halogen atoms or phenyl optionally substituted with alkyl, haloalkyl, alkoxy, haloalkoxy, alkylthio or halogen atoms; or represents a hydrogen atom; and $R^7$ represents a group defined for $R^9$ according to this characteristic or represents hydroxyl, halogen atoms, cyano, acyl, alkoxy, haloalkoxy or alkylthio; and $R^6$ represents a phenyl or aromatic heterocyclyl radical (preferably thiazolyl, isothiazolyl, thiadiazolyl, pyridyl or pyrimidinyl), optionally substituted with one or more substituents, which may be identical or different, and are chosen from hydroxyl, halogen atoms, cyano, acyl (preferably —C(=O)$R^c$, —C(=S)$R^c$ or —S(O)$_p R^c$, in which p represents 0, 1 or 2 and $R^c$ represents alkyl, haloalkyl, alkoxy, haloalkoxy, alkylthio, amino, monoalkylamino, dialkylamino or phenyl optionally substituted with alkyl, haloalkyl, alkoxy, haloalkoxy or alkylthio; or phenyloxy, phenylthio, carbocyclyl or heterocyclyl), amino, alkylamino, dialkylamino, alkyl, alkenyl, alkynyl, haloalkyl, $R^a$O-alkyl, acyloxyalkyl, cyanooxyalkyl, alkoxy, haloalkoxy, alkylthio, carbocyclyl (preferably cyclohexyl or cyclopentyl) optionally substituted with alkyl, haloalkyl, alkoxy, haloalkoxy or alkylthio; and benzyl optionally substituted with alkyl, haloalkyl, alkoxy, haloalkoxy or alkylthio.

According to one particularly preferred aspect of the invention, the invention relates to the compounds of general formula (I), and to the salts thereof, as defined above, which have the following characteristics taken separately or in combination:

$R^4$ represents a $C_1$–$C_{10}$ alkyl radical or a halogen atom;

m represents 1;

$R^5$ represents a $C_1$–$C_{10}$ alkyl radical or a halogen atom, and preferably occupies position 5 on the nucleus M;

A represents a direct bond or a divalent radical —O—, and occupies position 4 on the benzene nucleus M;

$R^6$ represents a phenyl radical optionally substituted with one or more substituents which may be halogens, alkyl, alkenyl, alkynyl, haloalkyl, alkoxyalkyl, hydroxyalkyl, haloalkoxyalkyl, alkoxy, alkylthio, acyl or cyano.

Complexes of the compounds according to the invention may be formed in the usual manner from a salt of formula NAn or NAn$_2$, in which N represents a metal cation, for example copper, manganese, cobalt, nickel, iron or zinc and An represents an anion, for example chloride, nitrate or sulphate.

The N-oxides of the compounds of the invention, when these compounds comprise a nitrogen atom which may be oxidized, are also included in the scope of the present invention.

When the compounds according to the invention exist in the form of E and Z geometrical isomers, the invention comprises the individual isomers and also mixtures thereof in all proportions.

When the compounds according to the invention exist in the form of tautomeric isomers, the invention comprises the individual tautomeric isomers and also mixtures thereof in all proportions.

When the compounds according to the invention exist in the form of optical isomers, the invention comprises the individual isomers and also mixtures thereof in all proportions, including the 50:50 mixture, known as the racemic mixture.

Any alkyl group defined above may be linear or branched and generally comprises from 1 to 10 carbon atoms, preferably from 1 to 7 carbon atoms and more preferably from 1 to 5 carbon atoms.

All the alkenyl or alkynyl groups defined above may be linear or branched, preferably comprise from 2 to 7 carbon atoms and generally contain up to 3 double or triple bonds which may be conjugated, for example vinyl, allyl, butadienyl or propargyl.

The carbocyclyl groups may be saturated, unsaturated or aromatic and may be 3- to 8-membered. Saturated carbocyclyl groups that are preferred comprise cyclopropyl, cyclopentyl and cyclohexyl. Unsaturated carbocyclyl groups that are preferred comprise up to 3 double bonds. An aromatic carbocyclyl group preferred is phenyl. The term carbocyclic has the same definition in the present invention. Furthermore, the term carbocyclyl comprises any type of fused carbocyclyl group, such as naphthyl, phenanthryl, indanyl and indenyl.

The heterocyclyl groups may be saturated, unsaturated or aromatic and may be 3- to 7-membered, up to 4 of which members may be hetero atoms such as nitrogen, oxygen and sulphur. Thus, the term "heterocyclyl group" means, for example, furyl, thienyl, pyrrolyl, pyrrolinyl, pyrrolidinyl, imidazolyl, dioxolanyl, oxazolyl, thiazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridyl, piperidyl, dioxanyl, morpholino, dithianyl, thiomorpholino, pyridazinyl, pyrimidinyl, pyrazinyl, piperazinyl, sulpholanyl, tetrazolyl, triazinyl, azepinyl, oxazepinyl, thiazepinyl, diazepinyl and thiazolinyl.

Furthermore, the term heterocyclyl comprises fused heterocyclyl groups, for example benzimidazolyl, benzoxazolyl, imidazopyridinyl, benzoxazinyl, benzothiazinyl, oxazolopyridyl, benzofuryl, quinolinyl, quinazolinyl, quinoxalinyl, dihydroquinazolinyl, benzothiazolyl, phthalimido, benzofuryl, benzodiazepinyl, indolyl and isoindolyl. The term heterocyclic has the same definitions.

The adjective "substituted" qualifying the alkyl, alkenyl, alkynyl, carbocyclyl and heterocyclyl groups means that these groups may be substituted with one or more substituents, which may be identical or different, chosen from: hydroxyl, alkenyl, alkynyl, mercapto, azido, nitro, halogens, cyano, acyl, alkoxycarbonyl, optionally substituted aminocarbonyl, optionally substituted amino, optionally substituted ammonio, optionally substituted carbocyclyl, optionally substituted heterocyclyl, cyanato, thiocyanato, —$SF_5$; —$OR^a$; —$SR^a$; —$SOR^a$; —$SO_2R^a$ and —$Si(R^a)_3$, with $R^a$ being alkyl, alkenyl, alkynyl, carbocyclyl or heterocyclyl, each of which may be optionally substituted. For the carbocyclyl and heterocyclyl groups, the list furthermore comprises alkyl, alkenyl and alkynyl, each of which may be optionally substituted. Preferred substituents for the alkyl, alkenyl or alkynyl radicals are: alkoxy, haloalkoxy or alkylthio, each of which contains from 1 to 5 carbon atoms; halogen; or optionally substituted phenyl. Preferred substituents for the carbocyclyl and heterocyclyl groups are alkyl, haloalkyl, alkoxy, haloalkoxy or alkylthio, each of which contains from 1 to 5 carbon atoms; halogen; or optionally substituted phenyl.

For the alkyl radicals and the carbon atoms of the carbocyclyl and heterocyclyl groups, the list comprises divalent radicals such as oxo or imino, optionally substituted with optionally substituted amino, $R^a$ or —$OR^a$ (in which $R^a$ is as defined above). Preferred radicals are oxo, imino, alkylimino, oximino, alkyloximino or hydrazono.

The amino groups, when they are substituted and where appropriate, may be substituted with one or two identical or different substituents chosen from: alkyl, alkenyl, optionally substituted alkynyl, optionally substituted amino, —$OR^a$ (in which $R^a$ is as defined above), carbocyclyl, heterocyclyl and acyl. According to another aspect, two substituents, with the nitrogen atom to which they are attached, may form a heterocyclyl group, preferably a 5- to 7-membered heterocyclyl group, which may be substituted and which may contain other heteroatoms, for example morpholino, thiomorpholino or piperidyl.

The term "acyl" comprises the residues of sulphur-containing acids and phosphorus-containing acids and also carboxylic acids. The said residues are thus included in the general formulae: —$C(=X^a)R^b$, —$S(O)_pR^b$ and —$P(=X^a)(OR^a)(OR^a)$, in which, appropriately, $X^a$ represents O or S, $R^b$ is as defined for $R^a$, —$OR^a$, —$SR^a$, optionally substituted amino or acyl; and p represents 1 or 2. Preferred groups are —$C(=O)R^c$, —$C(=S)R^c$ and —$S(O)_pR^c$ in which $R^c$ represents alkyl, $C_1$–$C_5$ alkoxy, $C_1$–$C_5$ alkylthio, phenyl, phenyloxy, phenylthio, carbocyclyl, heterocyclyl or amino, each of which may be optionally substituted.

The compounds according to the invention are useful as fungicides and control the pathogens of the families Deuteromycetes, Oomycetes, Ascomycetes, Phycomycetes and Basidiomycetes. Antifungal activity is demonstrated on cereal diseases such as, for example:

SEPTORIA diseases of wheat (*Leptosphaeria nodorum* & *Septoria tritici*),

POWDERY MILDEWS (*Erysiphe graminis f.sp.* and *Erysiphe graminis f.sp tritici*), wheat RUSTS (*Puccinia recondita, Puccinia striiformis*), wheat EYE SPOT (*Pseudocercosporella herpotrichoides*), NET BLOTCH of barley (*Drechslera teres*) and LEAF BLOTCH of barley (*Rhynchosporiose secalis*). Similarly:

MILDEWS of solanaceae (*Phytophthora infestans*) and of vine (*Plasmopara viticola*), GREY MOLD (*Botrytis cinerea*), rice diseases (BLAST, BLIGHT and SHEATH SPOT) are controlled.

Thus, the present invention also provides a method for combating phytopathogenic fungi at a site which is infested or liable to be infested with them, which comprises the application at this site of a compound of formula (I) or a salt thereof.

The invention also provides an agricultural composition comprising a compound of formula (I) or a salt thereof mixed with an agriculturally acceptable diluent or support.

Needless to say, the composition according to the invention may comprise more than one compound according to the invention.

Furthermore, the composition may comprise one or more additional active materials, for example compounds known to have growth-regulatory properties on plants, or herbicidal, fungicidal, insecticidal, acaricidal, antimicrobial or antibacterial properties. The compound according to the invention may thus be used, for example, simultaneously, sequentially or alternately with the other active material(s).

The diluent or support in the composition according to the invention may be a solid or a liquid in combination with a surfactant, for example a dispersant, an emulsifier or a wetting agent. Surfactants that are suitable comprise anionic compounds such as a carboxylate, for example a metal carboxylate of a long-chain fatty acid; an N-acylsarcosinate; mono- or diesters of phosphoric acid with ethoxides of fatty alcohols or ethoxides of an alkyl phenol, or salts of such esters; fatty alkyl sulphates such as sodium dodecyl sulphate, sodium octadecyl sulphate or sodium cetyl sulphate; ethoxylated fatty alkyl sulphates; ethoxylated alkylphenyl sulphates; lignin sulphonates, petroleum sulphonates; alkylaryl sulphonates such as alkylbenzene sulphonates or lower alkylnaphthalene sulphonates, for example butylnaphthalene sulphonate; condensates of naphthalene sulphone-formaldehyde salts; condensates of phenyl sulphone-formaldehyde salts; or more complex sulphonates such as amide sulphonates, for example the product of condensation of oleic acid and of sulphonated N-methyltaurine; dialkyl sulphosuccinates, for example the sodium sulphonate of dioctyl succinate; acidic derivatives of alkylglycoside and alkylpolyglycoside compounds and metal salts thereof, for example alkylpolyglycoside citrate or tartrate; or mono-, di- and trialkyl esters of citric acid, and metal salts thereof.

Nonionic agents comprise products of condensation of fatty acid esters, of fatty alcohols, of fatty acid amides or of phenols substituted with fatty alkyls or fatty alkenyls, with ethylene oxide and/or propylene oxide; fatty esters of polyhydric alcohol ethers, for example fatty acid esters of sorbitan; products of condensation of such esters with ethylene oxide, for example polyoxyethylene fatty acid esters of sorbitan; alkyl glycoside products, alkyl polyglycoside products; block copolymers of ethylene oxide and of propylene oxide; acetylenic glycols such as 2,4,7,9-tetramethyl-5-decyne-4,7-diol; ethoxylated acetylenic glycols; grafted copolymers containing acrylic chain units; alkoxylated siloxane surfactants; or surfactants of imidazoline type, for example 1-hydroxyethyl-2-alkylimidazoline.

Examples of cationic surfactants comprise, for example, a monoamine, a diamine or a polyamine, in acetate, naphthenate or oleate form; an amine containing oxygen, for instance an amine oxide, a polyoxyethylene-alkylamine or a polyoxypropylene-alkylamine; an amine linked to an amide prepared by condensation of a carboxylic acid with a diamine or a polyamine; or a quaternary ammonium salt.

The compositions according to the invention may take any form in the field of formulation of agrochemical compounds, for example solution, aerosol, dispersion, aqueous emulsion, microemulsion, dispersible concentrate, sprayable powder, composition for covering or coating seeds, composition for fumigation or for smoking, dispersible powder, emulsifiable concentrate, granulates or impregnated strip. Furthermore, they may be in a form which is suitable for direct application or as a primary composition or concentrate requiring dilution with a suitable amount of water or of another diluent before application.

A dispersible concentrate comprises a compound according to the invention dissolved in one or more solvents that are fully or partially water-soluble, and one or more surfactants and/or polymers. Addition of the formulation to water causes a crystallization of the active material, the process being controlled by the surfactants and/or polymers, leading to a fine dispersion.

A sprayable powder comprises a compound according to the invention mixed and intimately ground with a pulverulent solid diluent, for example kaolin.

An emulsifiable concentrate comprises a compound according to the invention dissolved in a water-immiscible solvent and which forms an emulsion or a microemulsion when added to water in the presence of an emulsifier.

A solid granulate comprises a compound according to the invention combined with diluents similar to those which may be used for the sprayable powders, the mixture in this case being granulated according to known methods. According to one alternative, the solid granulate comprises the active material absorbed or coated onto a preformed granular support, for example Fuller's earth, attapulgite, silica or limestone grit.

The wettable powders, granules or granulates usually comprise the active material as a mixture with suitable surfactants and a diluent made of inert powder such as clay or diatomaceous earth.

Another concentrate which is suitable is a pourable concentrated suspension formed by grinding the compound with water or another liquid, surfactants and a suspension agent.

The concentration of the active material in the composition of the present invention, as applied to the plants, is preferably between 0.0001 and 1.0 per cent by weight and particularly between 0.0001 and 0.01 per cent by weight. In a primary composition, the amount of active material may vary within a wide range and may be, for example, between 5 and 95 per cent by weight of composition.

When it is used, a compound of the invention is generally applied to the seeds, the plants or their habitat. Thus, the compound may be applied directly to the soil before, at the time of or after seeding, such that the presence of the active material in the soil can control the growth of the fungi which may attack the seeds. During a direct treatment of the soil, the active material may be applied in any manner whatsoever which allows it to be intimately mixed with the soil, such as by spraying, by spreading granules in solid form or by applying the active material at the same time as the seed using it in the same seeder as the seeds. A suitable application rate is between 5 and 1000 g per hectare and more preferably between 10 and 500 g per hectare.

Alternatively, the active material may be applied directly to the plant, for example by spraying or dusting either at the moment the fungus begins to appear on the plant or before the appearance of the fungus as a protective measure. In both these cases, the preferred method of application is spraying onto the leaves. It is generally important to gain effective control against fungi at the early stages of growth of the plant, since this is the stage at which the plant may be the most severely damaged. However, if this is necessary, the spraying or dusting may conveniently contain a pre-emergence or post-emergence herbicide. Occasionally, it is feasible to treat the roots, bulbs, tubers or other vegetal outgrowths of a plant before or during planting, for example by dipping the roots in a suitable solid or liquid composition. When the active material is applied directly to the plant, a suitable application rate is between 0.025 and 5 kg per hectare and preferably between 0.05 and 1 kg per hectare.

Furthermore, the compounds according to the invention may be applied to harvested fruit, legumes or seeds to prevent infection during storage.

Furthermore, the compounds according to the invention may be applied to plants or plant parts which have been genetically modified.

Furthermore, the compounds according to the invention may be used to treat fungal infections in lumber and for application to public health. The compounds according to the invention may also be used to treat fungal infections on pets or farm animals.

Compounds according to the invention may be prepared by many routes, according to known processes.

Thus, the compounds of general formula (I) may be prepared, for example, from compounds of general formula (II) according to Scheme 1 below:

Scheme 1

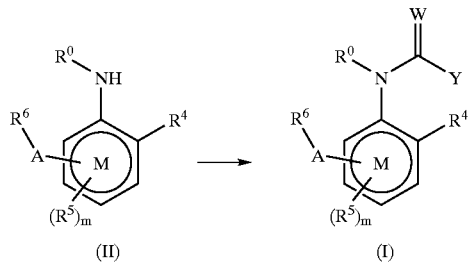

The following reaction conditions may be used to convert compounds of formula (II) into compounds of formula (I):

in general, reaction with Cl(CW)Y, that is to say a carbamoyl chloride when W represents O and Y represents —NR$^1$R$^2$, a thiocarbamoyl chloride when W represents S and Y represents —NR$^1$R$^2$, a chloroformate when W represents O and Y represents —OR$^3$, a chlorothionoformate when W represents S and Y represents —OR$^3$, a chlorothiolformate when W represents O and Y represents —SR$^3$ or a chlorodithioformate when W represents S and Y represents —SR$^3$;

when R$^0$ represents a hydrogen atom and W represents O, reaction with phosgene, diphosgene or triphosgene to form the isocyanate, followed by treatment with HY;

when R$^0$ represents a hydrogen atom and W represents S, reaction with thiophosgene to form the isothiocyanate, followed by treatment with HY;

when Y represents —NHR$^1$, reaction with R$^1$N═(CW);

when W represents S, Y represents —SR$^3$ and R$^0$ is other than a hydrogen atom, reaction with carbon disulphide and R$^3$X, X representing a halogen atom or any other leaving group.

Furthermore, compounds of general formula (I) may be converted into other compounds of general formula (I) by derivatization of the radicals R$^0$ or R$^1$ or R$^2$ or R$^3$; or by acylation, cyanation or alkylation when W represents O and R$^0$ or R$^1$ or R$^2$ or R$^3$ represent a hydrogen atom;

When R$^0$ is other than a hydrogen atom, compounds of general formula (II) may be prepared from compounds of general formula (III) according to Scheme 2 below:

Scheme 2

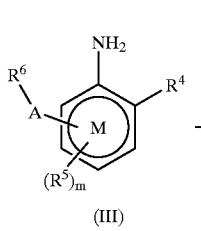 → 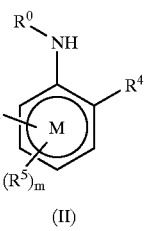

(III)    (II)

The following reaction conditions may be used to carry out the conversion:
- when R$^0$ represents an alkyl radical, formylation or acylation with an anhydride, followed by a reduction with borane/dimethyl sulphide;
- when R$^0$ represents a cyano radical, cyanation with cyanogen chloride or bromide;
- when R$^0$ represents an acyl radical, acylation with an acyl halide.

The compounds of general formula (III) may be prepared by reducing the nitro radical of the compounds of formula (IV) according to Scheme 3. The preferred reaction conditions comprise a reaction with hydrazine hydrate in ethanol catalysed with palladium or platinum;

Scheme 3

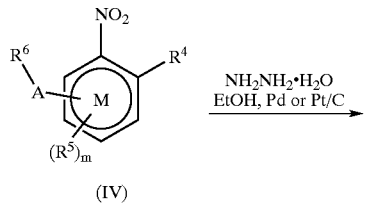 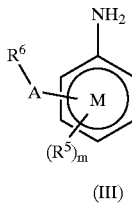

(IV)    (III)

The compounds of formula (IIIa), that is to say the compounds of general formula (III) in which A represents a direct bond, may be prepared according to Scheme 4, in which X$^v$ represents a leaving group:

Scheme 4

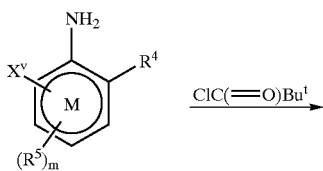

-continued

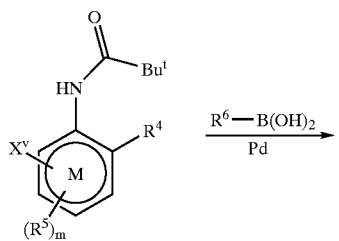

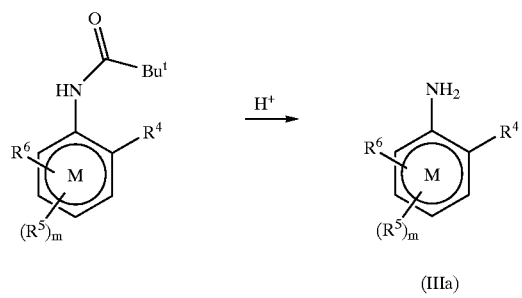

(IIIa)

The compounds of formula (IIIb), that is to say the compounds of general formula (III) in which R$^4$ represents a halogen atom, may be prepared according to Scheme 5, in which X$^T$ represents a halogen atom. When X$^T$ represents bromine, the preferred reaction conditions comprise stirring with bromine in a suitable solvent.

Scheme 5

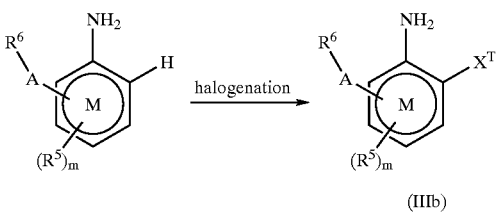

(IIIb)

The compounds of formula (IIIc), that is to say the compounds of general formula (III) in which A represents NHC(=O)—; the compounds of formula (IIId), that is to say the compounds of formula (III) in which A represents a direct bond and R$^6$ represents an optionally substituted phthalimido radical, in which the curved line connecting positions 3 and 4 of the phthalimido radical represents an optionally substituted carbocyclic chain; and the compounds of formula (IIIe), that is to say the compounds of general formula (III) in which A represents a direct bond and R$^6$ represents a pyrrolyl radical, optionally substituted in positions 2 and 5 with one or more radicals R which may be identical or different; may be prepared from compounds of formula (V) according to the methodology given in Scheme 6. For certain compounds of formula (V), the protection/deprotection of the amino radical located ortho to the radical R$^4$ may be required in order to improve the yields.

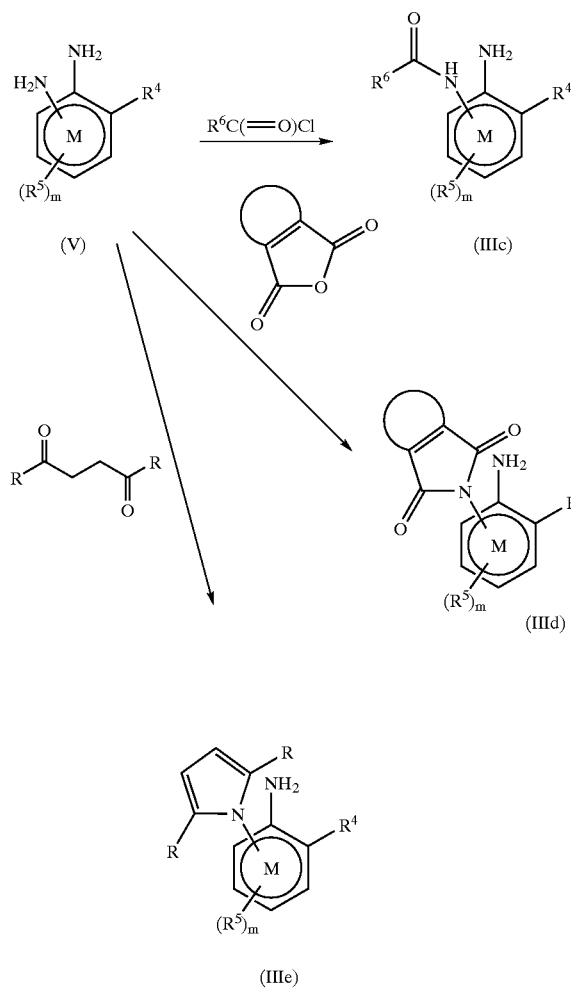

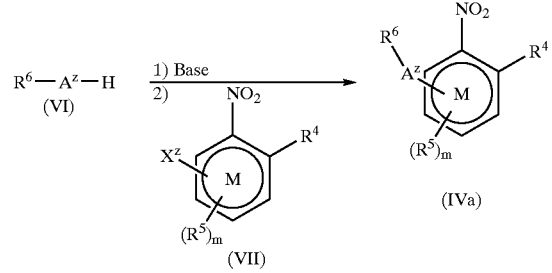

The compounds of formula (IVa), that is to say the compounds of general formula (IV) in which A represents a radical $A^z$, may be prepared by reacting the compounds of formula (VI) with the compounds of formula (VII) according to Scheme 7. $A^z$ represents a radical which, in compound (VI) forms an anion under basic conditions. Alternatively, $A^z$ represents a basic primary or secondary nitrogen atom. $X^z$ represents a leaving group, preferably a halogen atom. When $A^z$ represents an oxygen atom, preferred reaction conditions comprise the treatment of (VI) with sodium hydride, followed by addition of (VII). When $A^z$ represents a sulphur atom, the preferred reaction conditions comprise the reaction of (VI) with (VII) in the presence of a tertiary amine base such as ethyldiisopropylamine. When $A^z$ represents —CHR$^7$—, the preferred reaction conditions comprise the treatment of (VI) with potassium tert-butoxide in dimethylformamide at low temperature. When $A^z$ represents a basic nitrogen atom, no base is required.

The compounds of formula (IVb), that is to say the compounds of general formula (IV) in which A represents a radical $A^W$, may be prepared by reacting compounds of formula (VIII) with the compounds of formula (IX) according to Scheme 8. $A^W$ represents a radical which, in a compound (VIII), forms an anion under basic conditions. $X^W$ represents a leaving group, preferably a halogen atom. Preferred basic conditions comprise the reaction of (VIII) with potassium carbonate, sodium carbonate or sodium hydride, followed by the addition of (IX).

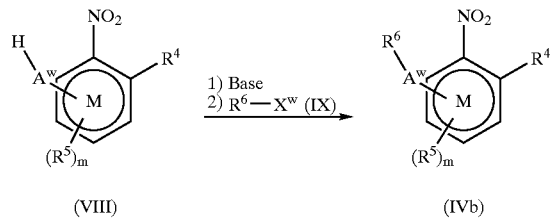

The compounds of formula (IVc), that is to say the compounds of general formula (IV) in which A represents O, may be prepared by reacting compounds of formula (X) with boronic acids of formula (XI) according to Scheme 9. The preferred reaction conditions comprise a reaction with copper acetate and triethylamine.

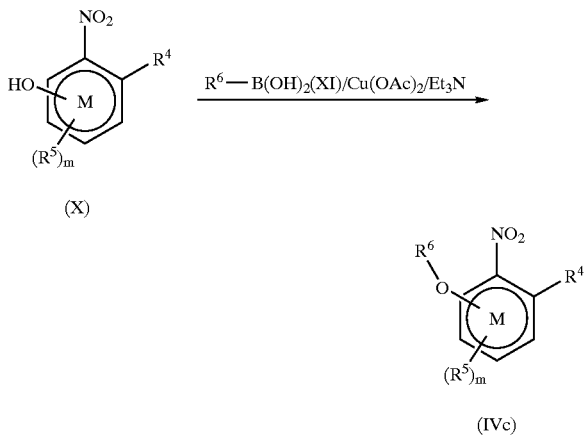

The compounds of formula (IVd), that is to say the compounds of formula (IV) in which A represents a direct bond, may be prepared according to Scheme 10 from compounds of formula (XII) in which $X^Z$ represents a leaving group, preferably a halogen atom.

Scheme 10

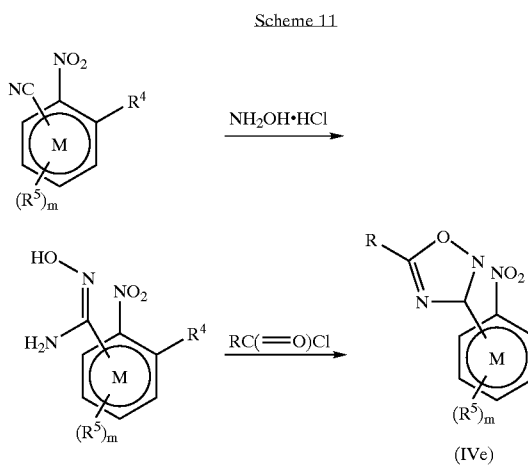

(XII)    (IVd)

The compounds of formula (IV) in which A represents a direct bond and $R^6$ represents a heterocyclyl radical, may be prepared using several methods known to those skilled in the art (see, for example, "Comprehensive Heterocyclic Chemistry", Vols 1–7, A. R. Katritzky and C. W. Rees). By way of example, the routes of access to the compounds of formula (IV) containing a 1,2,4-oxadiazol-3-yl radical [compound (IVe)] and a 1,3,4-oxadiazol-2-yl radical [compound (IVf)] are given in Schemes 11 and 12.

Scheme 11

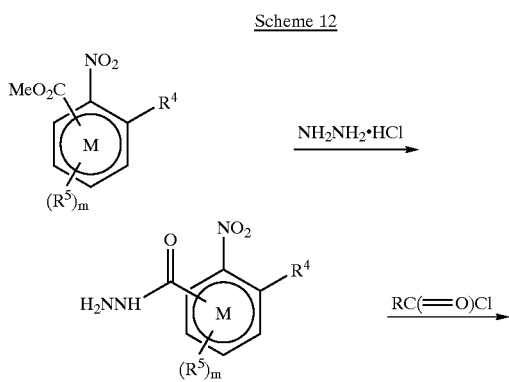

(IVe)

Scheme 12

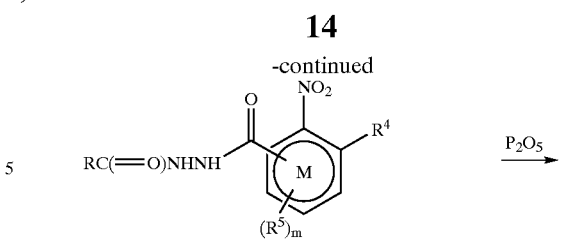

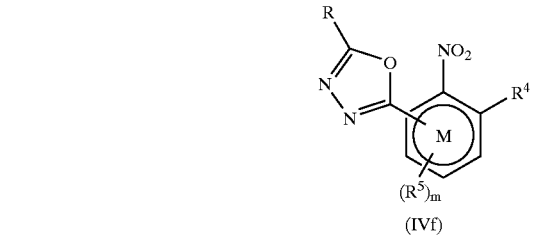

(IVf)

The compounds of formula (IIIf), that is to say the compounds of general formula (III) in which A represents —CHR$^7$— with $R^7$ representing a hydroxyl or alkoxy radical, may be prepared from compounds of formula (IIIg) according to the methodology described in Scheme 13, in which R represents an optionally substituted alkyl radical or a hydrogen atom, and in which $R^6$ represents an optionally substituted carbocyclic or heterocyclic radical which may form an anion under basic conditions.

Similarly, the reaction sequence described in Scheme 13 may be carried out on the compounds of formula (IIIf) in which the amine function is replaced with a precursor of the said function, for example an —NO$_2$ radical or a radical —N(CW)R$_0$.

Scheme 13

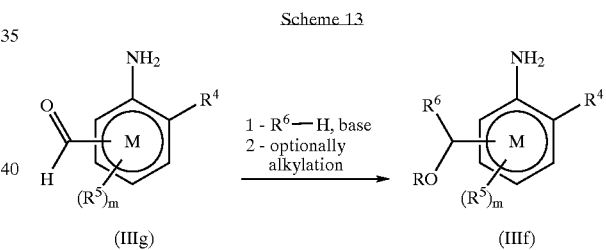

(IIIg)    (IIIf)

Alternatively, using chemistry similar to that described above, the compounds of general formula (I) may be prepared by introducing $R^6$ after the formation of the species —NR$_0$(CW)Y.

Other methods for gaining access to the compounds of formula (I), and also to intermediates thereof and starting materials, will appear obvious to those skilled in the art, such as those described, for example, in Brown, B. R. *The Organic Chemistry of Aliphatic Nitrogen Compounds* (Oxford Science Publications, 1994) and Patai, S. *"The chemistry of cyanates and their thio derivatives"* (John Wiley & Sons, 1977).

Furthermore, the compounds according to the invention may be prepared using the well-known techniques of combinatorial chemistry.

The invention is illustrated by the following examples, but should not be understood as being limited thereby. The structures of the novel compounds isolated were confirmed by NMR and/or other suitable analyses. The proton NMR ($^1$H NMR) spectra were recorded in deuterochloroform and the chemical shifts (δ) are given in parts per million relative to tetramethylsilane.

EXAMPLE 1

N'-(4-{[3-(1,1-dimethylethyl)phenyl]oxy}-2,5-dimethylphenyl)-N-ethyl-N-methylthiourea (Compound 27)

Ethylmethylamine (450 mg) is added dropwise to a solution of 1-{[3-(1,1-dimethylethyl)phenyl]oxy}-4-isothiocyanato-2,5-dimethylbenzene (1.9 g) in tetrahydrofuran (6 ml) at 0° C. The reaction mixture obtained is stirred at room temperature for 1 h and then concentrated and triturated with heptane. The title product is obtained in the form of a white precipitate.

Preparation of the Starting Materials 1-Chloro-2,5-dimethyl-4-nitrobenzene

A sulphonitric mixture at 0° C., composed of sulphuric acid (3.8 ml) and nitric acid (1 ml), is added dropwise to a mixture, cooled to 10° C., of 2-chloro-1,4-xylene (1.4 g), acetic acid (17 ml) and 98% sulphuric acid (1 ml). The reaction medium is poured into a water/ice mixture and then filtered. The yellow precipitate is recrystallized from petroleum ether to give the title compound.

1-{[3-(1,1-Dimethylethyl)phenyl]oxy}-2,5-dimethyl-4-nitrobenzene 3-t-Butylphenol (7.5 g) and potassium carbonate (6.9 g) are added to a solution of 1-chloro-2,5-dimethyl-4-nitrobenzene (9.5 g) in dimethylformamide (60 ml) under an inert atmosphere. The reaction mixture obtained is refluxed for 5 h and then partitioned in a water/diisopropyl ether mixture. The organic phase is washed with a basic aqueous solution and then with water at pH 7. Drying over magnesium sulphate and then addition of carbon black, followed by filtration through Celite gives, after concentration, the title product.

4-{[3-(1,1-Dimethylethyl)phenyl]oxy}-2,5-dimethyl-aniline

Hydrazine hydrate (4.3 ml) is added dropwise to a mixture of 1-{[3-(1,1-dimethylethyl)phenyl]oxy}-2,5-dimethyl-4-nitrobenzene (8.65 g) and 5% palladium-on-charcoal (100 mg) in n-propanol (60 ml) heated to 90° C. The reaction mixture is maintained at 90° C. for 2 h and then filtered through Celite. Concentration gives the title compound.

1-{[3-(1,1-Dimethylethyl)phenyl]oxy}-4-isothiocyanato-2,5-dimethylbenzene

Thiophosgene (0.38 ml) is added to a two-phase mixture at room temperature of 4-((3-(1,1-dimethyl-ethyl)phenyl)oxy)-2,5-dimethylaniline (1.35 g) in toluene (6 ml) and sodium bicarbonate (840 mg) in water (6 ml). The reaction mixture obtained is stirred for 2 h and the phases are then separated by settling. The aqueous phase is extracted with toluene and the combined organic phases are then washed with water, dried (magnesium sulphate) and then concentrated to give the title product.

The procedure described for the synthesis of N'-(4-((3-(1,1-dimethylethyl)phenyl)oxy)-2,5-dimethylphenyl)-N-ethyl-N-methylthiourea was generalized to other amines and transposed to other temperature conditions and solvents, in particular acetonitrile, diethyl ether and dimethylformamide. This procedure was also used for the synthesis of thiosemicarbazides and thiohydroxylureas.

In the case of 1-(4-{[3-(1,1-dimethyl-ethyl)phenyl]oxy}-2,5-dimethylphenyl)-1,3-dihydro-2H-imidazole-2-thione (Compound 16), the cyclic thiourea was obtained by reacting, according to the procedure described above, aminoacetaldehyde dimethyl acetal with 4-{[3-(1,1-dimethylethyl)phenyl]oxy}-2,5-dimethylaniline.

The procedure described to prepare 4-{[3-(1,1-dimethylethyl)phenyl]oxy}-2,5-dimethylaniline was also used to prepare the following anilines: 4-[(3-chlorophenyl)oxy]-2,5-dimethylaniline, 4-{[4-chloro-3-(trifluoromethyl)phenyl]oxy}-2,5-dimethylaniline, 4-{[4-fluoro-3-(trifluoromethyl)phenyl]oxy}-2,5-dimethylaniline, 2,5-dimethyl-4-{[3-(trifluoromethyl)phenyl]oxy}aniline, 4-[(4-ethylphenyl)oxy]-2,5-dimethylaniline, 4-[(4-chlorophenyl)oxy]-2,5-dimethylaniline and 4-{[3-(1,1-dimethylethyl)phenyl]oxy}-2-(trifluoromethyl)aniline.

Other anilines used as intermediates in the synthesis of products illustrated were synthesized according to the following methods.

Preparation of 4-(5-(1,1-dimethylethyl)-1,3,4-oxadiazol-2-yl)-2-methylaniline Hydrazine hydrate (6.7 ml) is added to a solution at room temperature of methyl 3-methyl-4-nitrobenzoate (25 g) in methanol (300 ml). The reaction mixture is refluxed for 15 minutes and then cooled. The dried filtered precipitate corresponds to 3-methyl-4-nitrobenzhydrazide.

Water is added to a mixture consisting of 3-methyl-4-nitrobenzhydrazide (3.9 g), triethylamine (3 ml) and 2,2-dimethylpropanoyl chloride (2.6 ml) in dichloromethane (120 ml) stirred for 2 h. After drying, evaporation and trituration of the organic phase in petroleum ether, N'-(2,2-dimethylpropanoyl)-3-methyl-4-nitrobenzhydrazide is obtained in the form of a precipitate.

Phosphorus pentoxide (10 g) is added to a suspension of N'-(2,2-dimethylpropanoyl)-3-methyl-4-nitrobenzhydrazide (5.1 g) in toluene (200 ml). After refluxing for 2 h, the reaction mixture is poured into ice-water and extracted with diethyl ether. The organic phases are combined, dried over magnesium sulphate, evaporated and purified by chromatography on silica (eluent: 2/1 diethyl ether/petroleum ether) to give 2-(1,1-dimethylethyl)-5-(3-methyl-4-nitrophenyl)-1,3,4-oxadiazole.

A mixture of 2-(1,1-dimethylethyl)-5-(3-methyl-4-nitrophenyl)-1,3,4-oxadiazole (1.6 g), $FeCl_3.6H_2O$ (5 g) and zinc powder (4 g) in a dimethylformamide/water mixture (1/1, 25 ml) is heated at 100° C. for 30 minutes and then filtered through Celite. After dilution with saturated aqueous sodium carbonate solution, the reaction mixture is extracted with diethyl ether. Drying over magnesium sulphate and evaporation of the organic phase gives the title aniline.

Preparation of 2,5-dimethyl-4-[(3-phenyl-1,2,4-thiadiazol-5-yl)oxy]phenylamine 4-Amino-2,5-dimethylphenol (10.5 g) is added at room temperature to a suspension of sodium hydride (60% dispersion in mineral oil, 3 g) in anhydrous dimethylformamide (300 ml). The reaction mixture is stirred for 30 minutes and 5-bromo-3-phenyl-1,2,4-thiadiazole (18 g) prepared according to Chem. Ber. 1961, 94, 2043 is then added slowly. After stirring for 15 h, the reaction mixture is diluted in ice-water and then extracted with diethyl ether. Drying over magnesium sulphate followed by concentration of the combined organic phases gives the title compound.

Preparation of 4-[3,4-dihydro-2(1H)-isoquinolinyl]-2,5-dimethylaniline

A mixture of 1-chloro-2,5-dimethyl-4-nitrobenzene (1.65 g) and 1,2,3,4-tetrahydroisoquinoline (5 ml) in N-methylpyrrolidine (5 ml) is stirred at 140° C. for 15 h. Dilution in water followed by extraction with diethyl ether and chromatography on silica (eluent: 1/1 petroleum ether/diethyl ether) of the dried and evaporated organic phase gives 2-(2,5-dimethyl-4-nitrophenyl)-1,2,3,4-tetrahydroisoquinoline.

2-(2,5-Dimethyl-4-nitrophenyl)-1,2,3,4-tetrahydroisoquinoline is reduced according to the methods illustrated above to give the title aniline.

Preparation of 4-(1-benzo-2-thienyl)-2,5-dimethyl-aniline

A mixture of 1-bromo-2,5-dimethyl-4-nitrobenzene (3.6 g), (1-benzo-2-thienyl)boronic acid (3.6 g), tetrakis(triphenylphosphine)palladium (0.4 g) and aqueous sodium carbonate solution (2M) (17 ml) in ethanol (36 ml) and toluene (100 ml) is stirred at reflux for 18 h. Partial evaporation followed by extraction with ethyl acetate, drying of the organic phase and then re-evaporation gives 2-(2,5-dimethyl-4-nitrophenyl)-1-benzothiophene.

2-(2,5-Dimethyl-4-nitrophenyl)-1-benzothiophene is reduced according to the methods described above to give the title aniline.

EXAMPLE 2

3-[4-(1-Benzo-2-thienyl)-2,5-dimethylphenyl]-2-thioxo-1,3-thiazolidin-4-one (Compound 3)

A solution of 2-(4-isothiocyanato-2,5-dimethylphenyl)-1-benzothiophene (0.22 g) and of ethyl sulphenyl acetate (0.09 g) in diethyl ether (2 ml) is stirred for 18 h at room temperature. The reaction medium is evaporated and then triturated in petroleum ether to give the title compound.

EXAMPLE 3

N-(4-{[4-Chloro-3-(trifluoromethyl)phenyl]oxy}-2,5-dimethylphenyl)-N,N'-diethyl-N'-methylurea (Compound 116)

One spatula of active charcoal and then diphosgene (2.07 g) are added to a solution of 4-{[4-chloro-3-(trifluoromethyl)phenyl]oxy}-2,5-dimethylaniline (3 g) in anhydrous ethyl acetate (50 ml) at 60° C. under argon. The reaction mixture obtained is heated at 60° C. for 1 h and then stirred at room temperature for 15 h. Filtration through Celite followed by evaporation and uptake of the residue in petroleum ether (50 ml) to which is added N-ethylmethylamine (1.12 g) gives, after evaporation, N'-(4-{[4-chloro-3-(trifluoromethyl)phenyl]oxy}-2,5-dimethylphenyl)-N-ethyl-N-methylurea. A 60% suspension of sodium hydride in mineral oil (46 mg) is added to a solution of the latter compound (380 mg) in tetrahydrofuran (2 ml), followed by addition of ethyl iodide (300 mg). The reaction mixture is stirred at 50° C. for 2 h and then diluted in water and extracted with diethyl ether. Drying of the organic phase over magnesium sulphate followed by evaporation gives the title compound.

The procedure described for the synthesis of N'-(4-{[4-chloro-3-(trifluoromethyl)phenyl]oxy}-2,5-dimethylphenyl)-N-ethyl-N-methylurea was generalized to other amines and transposed to other solvents, in particular acetonitrile, diethyl ether and dimethylformamide. Similar procedures were used for the synthesis of hydroxylureas, semicarbazides and carbamates.

The following examples (Table 1) illustrate, in a nonlimiting manner, a number of compounds according to the present invention and which were synthesized using the above procedures.

TABLE 1

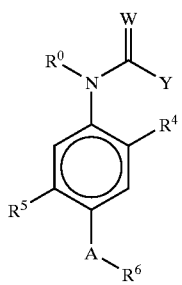

| Compound | R5 | R4 | W | R0 | Y | A | R6 |
|---|---|---|---|---|---|---|---|
| 1 | Me | Me | S | H | NEtMe | direct bond | 2-benzothienyl |
| 2 | Me | Me | S | H | NMe2 | direct bond | 2-benzothienyl |
| 3 | Me | Me | S | single bond with Y | —S\\\\/RO=O | direct bond | 2-benzothienyl |
| 4 | Me | Me | S | H | N-morpholino | direct bond | 2-benzothienyl |
| 5 | Me | Me | S | H | NHCH2Ph | direct bond | 2-benzothienyl |
| 6 | Me | Me | O | H | OEt | O | 3-tBu-phenyl |

TABLE 1-continued

| Compound | R5 | R4 | W | R0 | Y | A | R6 |
|---|---|---|---|---|---|---|---|
| 7 | Me | Me | S | single bond with Y | —S—CH₂—C(=O)—RO 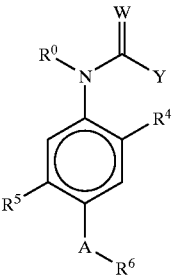 | O | 3-trifluoro-methylphenyl |
| 8 | H | Me | S | H | NHMe | direct bond | 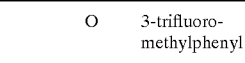 |
| 9 | H | Me | S | H | NH-cyclopropyl | direct bond | 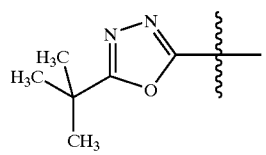 |
| 10 | H | Me | S | H | NHCH2Ph | direct bond | 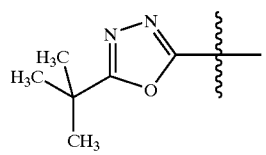 |
| 11 | H | Me | S | H | N-morpholino | direct bond | 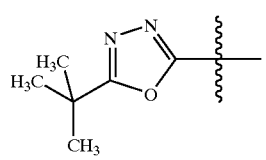 |
| 12 | Me | Me | O | H | OMe | direct bond | 2-benzothienyl |
| 13 | Me | Me | S | H | NHMe | direct bond | 2-benzothienyl |
| 14 | Me | Me | O | H | O-t-butyl | direct bond | 2-benzothienyl |
| 15 | H | Me | S | H | NHMe | direct bond | 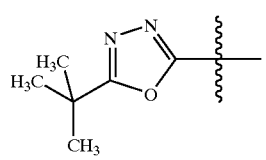 |
| 16 | Me | Me | S | single bond with Y | 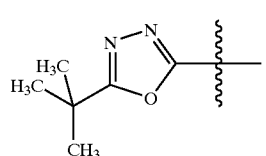 | O | 3-tBu-phenyl |

TABLE 1-continued

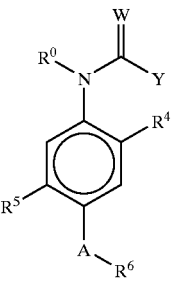

| Compound | R5 | R4 | W | R0 | Y | A | R6 |
|---|---|---|---|---|---|---|---|
| 17 | Me | Me | S | H | 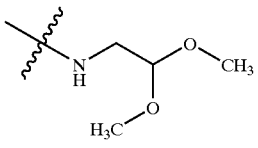 | O | 3-tBu-phenyl |
| 18 | Me | Me | S | H | 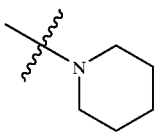 | O | 3-tBu-phenyl |
| 19 | Me | Me | S | H | NHEt | O | 3-tBu-phenyl |
| 20 | Me | Me | S | H | N-morpholino | O | 3-tBu-phenyl |
| 21 | Me | Me | S | H | NHiPr | O | 3-tBu-phenyl |
| 22 | Me | Me | S | H | NHnPr | O | 3-tBu-phenyl |
| 23 | Me | Me | S | H | Nhcyclopropyl | O | 3-tBu-phenyl |
| 24 | Me | Me | S | H | NMe2 | O | 3-tBu-phenyl |
| 25 | Me | Me | S | H | 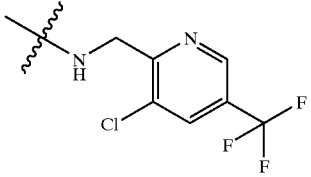 | O | 3-tBu-phenyl |
| 26 | Me | Me | S | H | 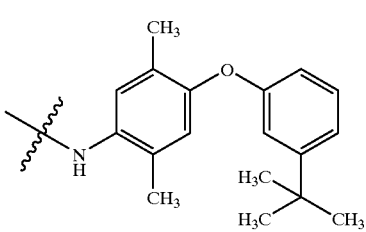 | O | 3-tBu-phenyl |
| 27 | Me | Me | S | H | NEtMe | O | 3-tBu-phenyl |
| 28 | Me | Me | S | H | NnBuMe | O | 3-tBu-phenyl |
| 29 | Me | Me | S | H | 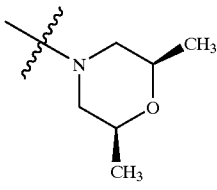 | O | 3-tBu-phenyl |
| 30 | Me | Me | S | H | NHMe | O | 4-Et-phenyl |

TABLE 1-continued

| Compound | R5 | R4 | W | R0 | Y | A | R6 |
|---|---|---|---|---|---|---|---|
| 31 | Me | Me | S | H | -NH-CH2-(benzo[1,3]dioxol-5-yl) | O | 3-tBu-phenyl |
| 32 | Me | Me | S | H | -NH-CH2-(1H-benzimidazol-2-yl) | O | 3-tBu-phenyl |
| 33 | Me | Me | O | H | O-tbutyl | O | 3-tBu-phenyl |
| 34 | Me | Me | S | H | -NH-CH2-(2,5-dimethoxy-2,5-dihydrofuran-2-yl) | O | 3-tBu-phenyl |
| 35 | Me | Me | S | H | -NH-CH2-(2,5-dimethoxy-2,5-dihydrofuran-2-yl) | O | 3-tBu-phenyl |
| 36 | Me | Me | S | H | -NH-CH2-(1-ethylpyrrolidin-2-yl) | O | 3-tBu-phenyl |
| 37 | Me | Me | S | H | NHMe | O | 4-chlorophenyl |
| 38 | Me | Me | O | H | NHiPr | O | 3-tBu-phenyl |
| 39 | Me | Me | O | Me | O-tbutyl | O | 3-tBu-phenyl |
| 40 | Me | Me | S | H | -N(CH3)-NH2 | O | 3-tBu-phenyl |

TABLE 1-continued

| Compound | R5 | R4 | W | R0 | Y | A | R6 |
|---|---|---|---|---|---|---|---|
| 41 | Me | Me | S | H | 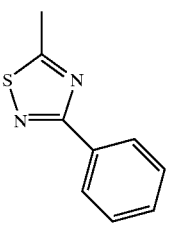 | O | 3-tBu-phenyl |
| 42 | Me | Me | S | H | NHMe | O | 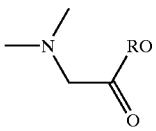 |
| 43 | Me | Me | S | H | NEtMe | O | 3-trifluoro-methylphenyl |
| 44 | Me | Me | S | single bond with Y | 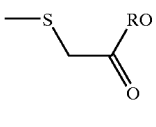 | O | 3-tBu-phenyl |
| 45 | Me | Me | S | single bond with Y | 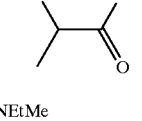 | O | 3-tBu-phenyl |
| 46 | Me | Me | S | single bond with Y | 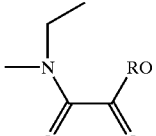 | O | 3-tBu-phenyl |
| 47 | H | CF3 | S | H | NEtMe | O | 3-tBu-phenyl |
| 48 | Me | Me | S | single bond with Y | 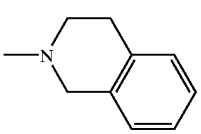 | O | 3-tBu-phenyl |
| 49 | Me | Me | O | H | Ome | O | 3-trifluoro-methylphenyl |
| 50 | Me | Me | S | H | NHMe | O | 3-tBu-phenyl |
| 51 | Me | Me | S | H | NHMe | direct bond |  |

TABLE 1-continued

| Compound | R5 | R4 | W | R0 | Y | A | R6 |
|---|---|---|---|---|---|---|---|
| 52 | Me | Me | S | single bond with Y | (structure) | O | 3-tBu-phenyl |
| 53 | Me | Me | S | single bond with Y | (structure) | O | 3-tBu-phenyl |
| 54 | Me | Me | S | single bond with Y | (structure) | O | 3-tBu-phenyl |
| 55 | Me | Me | S | single bond with Y | (structure) | O | 3-tBu-phenyl |
| 56 | Me | Me | S | single bond with Y | (structure) | O | 3-tBu-phenyl |
| 57 | Me | Me | O | H | NHPh | O | 3-trifluoromethylphenyl |
| 58 | Me | Me | S | H | NHPh | O | 3-trifluoromethylphenyl |

TABLE 1-continued
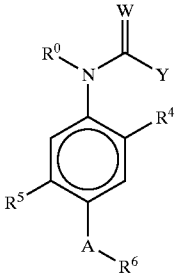
| Compound | R5 | R4 | W | R0 | Y | A | R6 |
|---|---|---|---|---|---|---|---|
| 59 | Me | Me | S | H | 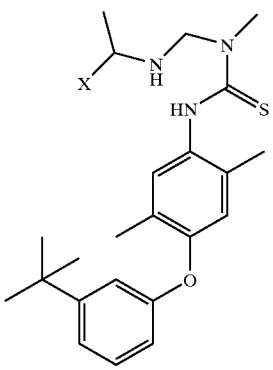 | O | 3-tBu-phenyl |
| 60 | Me | Me | O | H | N-morpholino | O | 3-tBu-phenyl |
| 61 | Me | Me | O | H | NetMe | O | 3-tBu-phenyl |
| 62 | Me | Me | O | H | 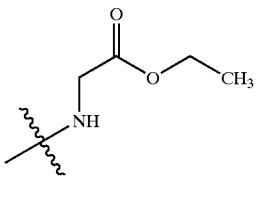 | O | 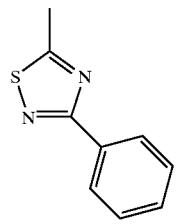 |
| 63 | Me | Me | O | single bond with Y | 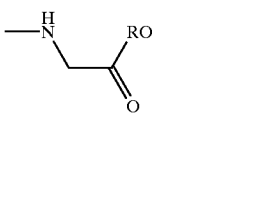 | O | 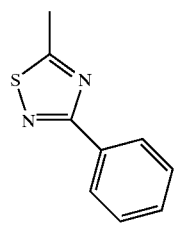 |
| 64 | Me | Me | S | H | NHPh | O | 3-tBu-phenyl |
| 65 | Me | Me | O | H | NEtMe | O | 4-chloro-3-trifluoro-methylphenyl |
| 66 | Me | Me | O | H | 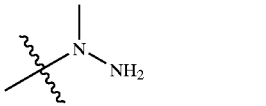 | O | 4-chloro-3-trifluoro-methylphenyl |

TABLE 1-continued

| Compound | R5 | R4 | W | R0 | Y | A | R6 |
|---|---|---|---|---|---|---|---|
| 67 | Me | Me | O | H | [NH-(2,5-dimethyl-4-(4-chloro-3-trifluoromethylphenoxy)phenyl)amino] | O | 4-chloro-3-trifluoro-methylphenyl |
| 68 | Me | Me | O | H | [NH-NH-C(O)-2-furyl] | O | 4-chloro-3-trifluoro-methylphenyl |
| 69 | Me | Me | O | H | [NH-morpholino] | O | 4-chloro-3-trifluoro-methylphenyl |
| 70 | Me | Me | O | H | [NH-NH-2-pyridyl] | O | 4-chloro-3-trifluoro-methylphenyl |
| 71 | Me | Me | O | H | [NH-NH-(2,5-dichlorophenyl)] | O | 4-chloro-3-trifluoro-methylphenyl |
| 72 | Me | Me | O | H | [NH-NH-SO2-phenyl] | O | 4-chloro-3-trifluoro-methylphenyl |
| 73 | Me | Me | O | H | [NH-NH-C(O)-NH-phenyl] | O | 4-chloro-3-trifluoro-methylphenyl |
| 74 | Me | Me | O | H | [NH-NH-C(O)-O-Me] | O | 4-chloro-3-trifluoro-methylphenyl |

TABLE 1-continued

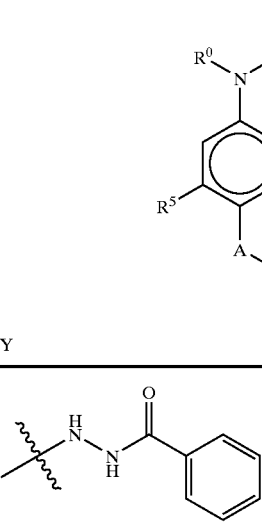

| Compound | R5 | R4 | W | R0 | Y | A | R6 |
|---|---|---|---|---|---|---|---|
| 75 | Me | Me | O | H | 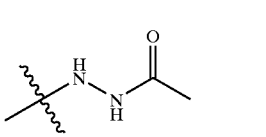 | O | 4-chloro-3-trifluoromethylphenyl |
| 76 | Me | Me | O | H | 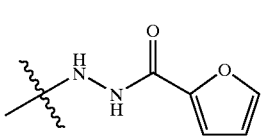 | O | 4-chloro-3-trifluoromethylphenyl |
| 77 | Me | Me | O | H | 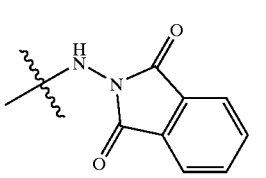 | O | 4-fluoro-3-trifluoromethylphenyl |
| 78 | Me | Me | O | H | 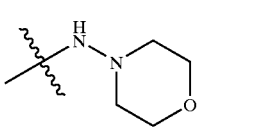 | O | 4-fluoro-3-trifluoromethylphenyl |
| 79 | Me | Me | O | H | 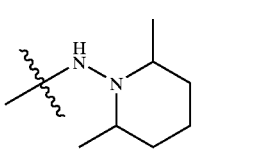 | O | 4-fluoro-3-trifluoromethylphenyl |
| 80 | Me | Me | O | H | 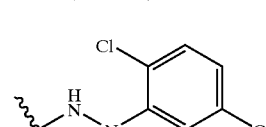 | O | 4-fluoro-3-trifluoromethylphenyl |
| 81 | Me | Me | O | H | 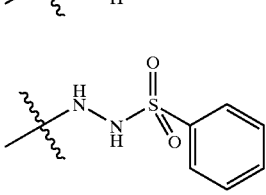 | O | 4-fluoro-3-trifluoromethylphenyl |
| 82 | Me | Me | O | H |  | O | 4-chloro-3-trifluoromethylphenyl |

TABLE 1-continued

| Compound | R5 | R4 | W | R0 | Y | A | R6 |
|---|---|---|---|---|---|---|---|
| 83 | Me | Me | O | H | -NH-NH-C(O)-NH-phenyl | O | 4-chloro-3-trifluoromethylphenyl |
| 84 | Me | Me | O | H | -NH-NH-C(O)-O-methyl | O | 4-chloro-3-trifluoromethylphenyl |
| 85 | Me | Me | O | H | -NH-NH-C(O)-phenyl | O | 4-chloro-3-trifluoromethylphenyl |
| 86 | Me | Me | O | H | -NH-NH-C(O)-CH3 | O | 4-chloro-3-trifluoromethylphenyl |
| 87 | Me | Me | O | H | -NH-N(CH3)2 | O | 4-chloro-3-trifluoromethylphenyl |
| 88 | Me | Me | O | H | -NH-NH-CH3 | O | 4-chloro-3-trifluoromethylphenyl |
| 89 | Me | Me | O | H | NHEt | O | 4-chloro-3-trifluoromethylphenyl |
| 90 | Me | Me | O | H | NHiPr | O | 4-chloro-3-trifluoromethylphenyl |
| 91 | Me | Me | O | H | NHcyclopropyl | O | 4-chloro-3-trifluoromethylphenyl |
| 92 | Me | Me | O | H | piperidin-1-yl | O | 4-chloro-3-trifluoromethylphenyl |
| 93 | Me | Me | O | H | -NH-CH2CH2-O-CH3 | O | 4-chloro-3-trifluoromethylphenyl |

TABLE 1-continued

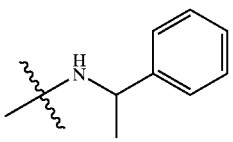

| Compound | R5 | R4 | W | R0 | Y | A | R6 |
|---|---|---|---|---|---|---|---|
| 94 | Me | Me | O | H | NHPh | O | 4-chloro-3-trifluoro-methylphenyl |
| 95 | Me | Me | O | H | NHCH2Ph | O | 4-chloro-3-trifluoro-methylphenyl |
| 96 | Me | Me | O | H | 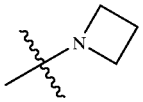 | O | 4-chloro-3-trifluoro-methylphenyl |
| 97 | Me | Me | O | H | 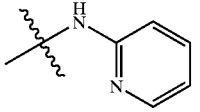 | O | 4-chloro-3-trifluoro-methylphenyl |
| 98 | Me | Me | O | H | N-morpholino | O | 4-chloro-3-trifluoro-methylphenyl |
| 99 | Me | Me | O | H | 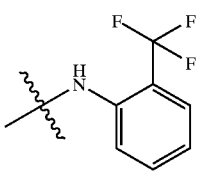 | O | 4-chloro-3-trifluoro-methylphenyl |
| 100 | Me | Me | O | H | 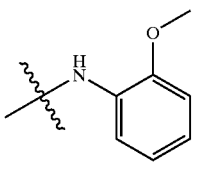 | O | 4-chloro-3-trifluoro-methylphenyl |
| 101 | Me | Me | O | H | 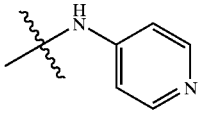 | O | 4-chloro-3-trifluoro-methylphenyl |
| 102 | Me | Me | O | H | 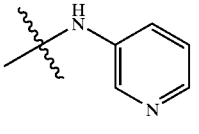 | O | 4-chloro-3-trifluoro-methylphenyl |
| 103 | Me | Me | O | H |  | O | 4-chloro-3-trifluoro-methylphenyl |

TABLE 1-continued

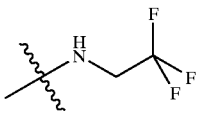

| Compound | R5 | R4 | W | R0 | Y | A | R6 |
|---|---|---|---|---|---|---|---|
| 104 | Me | Me | O | H | 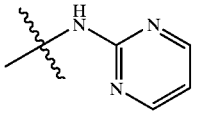 | O | 4-chloro-3-trifluoromethylphenyl |
| 105 | Me | Me | O | H | NMetBu | O | 4-chloro-3-trifluoromethylphenyl |
| 106 | Me | Me | O | H | 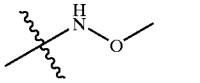 | O | 4-chloro-3-trifluoromethylphenyl |
| 107 | Me | Me | O | H | Ome | O | 4-chloro-3-trifluoromethylphenyl |
| 108 | Me | Me | O | H | Oet | O | 4-chloro-3-trifluoromethylphenyl |
| 109 | Me | Me | O | H | Oi-Pr | O | 4-chloro-3-trifluoromethylphenyl |
| 110 | Me | Me | O | H | OCH2Ph | O | 4-chloro-3-trifluoromethylphenyl |
| 111 | Me | Me | O | H | 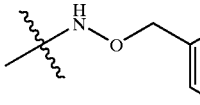 | O | 4-chloro-3-trifluoromethylphenyl |
| 112 | Me | Me | O | H | 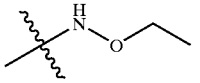 | O | 4-chloro-3-trifluoromethylphenyl |
| 113 | Me | Me | O | H | 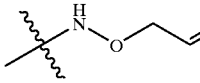 | O | 4-chloro-3-trifluoromethylphenyl |
| 114 | Me | Me | O | H | 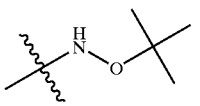 | O | 4-chloro-3-trifluoromethylphenyl |
| 115 | Me | Me | O | H |  | O | 4-chloro-3-trifluoromethylphenyl |
| 116 | Me | Me | O | Et | NEtMe | O | 4-chloro-3-trifluoromethylphenyl |

TABLE 1-continued

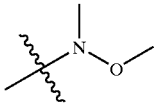

| Compound | R5 | R4 | W | R0 | Y | A | R6 |
|---|---|---|---|---|---|---|---|
| 117 | Me | Me | O | benzyl | NEtMe | O | 4-chloro-3-trifluoromethylphenyl |
| 118 | Me | Me | O | Me | NEtMe | O | 4-chloro-3-trifluoromethylphenyl |
| 119 | Me | Me | O | 3-propargyl | NEtMe | O | 4-chloro-3-trifluoromethylphenyl |
| 120 | Me | Me | O | 3-allyl | NEtMe | O | 4-chloro-3-trifluoromethylphenyl |
| 121 | Me | Me | O | (α-methyl)benzyl | NEtMe | O | 4-chloro-3-trifluoromethylphenyl |
| 122 | Me | Me | S | H | 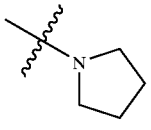 | O | 3-tbutyl-phenyl |
| 123 | Me | Me | S | H | N-thiazolidinyl | O | 3-tbutyl-phenyl |
| 124 | Me | Me | S | H | NMeiPr | O | 3-tbutyl-phenyl |
| 125 | Me | Me | S | H | NEt2 | O | 3-tbutyl-phenyl |
| 126 | Me | Me | S | H | NHCH2Ph | O | 3-tbutyl-phenyl |
| 127 | Me | Me | S | H | 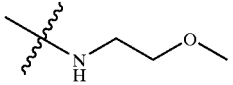 | O | 3-tbutyl-phenyl |
| 128 | Me | Me | S | H | 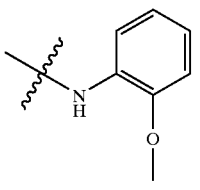 | O | 3-tbutyl-phenyl |
| 129 | Me | Me | S | H | 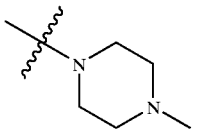 | O | 3-tbutyl-phenyl |
| 130 | Me | Me | S | H |  | O | 3-tbutyl-phenyl |

TABLE 1-continued

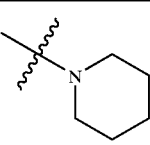

| Compound | R5 | R4 | W | R0 | Y | A | R6 |
|---|---|---|---|---|---|---|---|
| 131 | Me | Me | S | H | 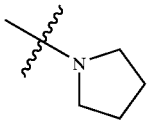 | O | 4-chloro-3-trifluoromethylphenyl |
| 132 | Me | Me | S | H | N-morpholino | O | 4-chloro-3-trifluoromethylphenyl |
| 133 | Me | Me | S | H | NEt2 | O | 4-chloro-3-trifluoromethylphenyl |
| 134 | Me | Me | S | H | NHCH2Ph | O | 4-chloro-3-trifluoromethylphenyl |
| 135 | Me | Me | S | H | 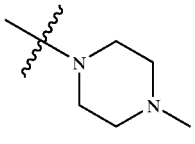 | O | 4-chloro-3-trifluoromethylphenyl |
| 136 | Me | Me | S | H | NHcyclopropyl | O | 4-chloro-3-trifluoromethylphenyl |
| 137 | Me | Me | S | H | 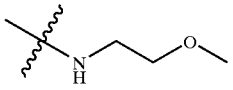 | O | 4-chloro-3-trifluoromethylphenyl |
| 138 | Me | Me | S | H | 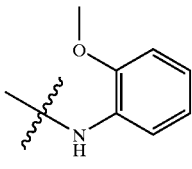 | O | 4-chloro-3-trifluoromethylphenyl |
| 139 | Me | Me | S | H | 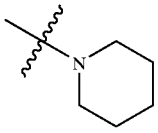 | O | 4-chloro-3-trifluoromethylphenyl |
| 140 | Me | Me | S | H |  | O | 4-fluoro-3-trifluoromethylphenyl |
| 141 | Me | Me | S | H | N-morpholino | O | 4-fluoro-3-trifluoromethylphenyl |

TABLE 1-continued

| Compound | R5 | R4 | W | R0 | Y | A | R6 |
|---|---|---|---|---|---|---|---|
| 142 | Me | Me | S | H | NEt2 | O | 4-fluoro-3-trifluoromethylphenyl |
| 143 | Me | Me | S | H | NHCH2Ph | O | 4-fluoro-3-trifluoromethylphenyl |
| 144 | Me | Me | S | H | pyrrolidin-1-yl | O | 4-fluoro-3-trifluoromethylphenyl |
| 145 | Me | Me | S | H | NHcyclopropyl | O | 4-fluoro-3-trifluoromethylphenyl |
| 146 | Me | Me | S | H | 4-methylpiperazin-1-yl | O | 4-fluoro-3-trifluoromethylphenyl |
| 147 | Me | Me | S | H | NHiPr | O | 4-fluoro-3-trifluoromethylphenyl |
| 148 | Me | Me | S | H | NH-CH2CH2-OMe | O | 4-fluoro-3-trifluoromethylphenyl |
| 149 | Me | Me | S | H | NEtMe | O | 4-fluoro-3-trifluoromethylphenyl |
| 150 | Me | Me | S | H | NH-(2-methoxyphenyl) | O | 4-fluoro-3-trifluoromethylphenyl |
| 151 | Me | Me | S | H | NH-CH(Me)Ph | O | 4-fluoro-3-trifluoromethylphenyl |
| 152 | Me | Me | S | H | NH-CH2CH2-NMe2 | O | 3-tbutyl-phenyl |

TABLE 1-continued

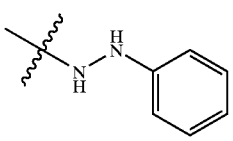

| Compound | R5 | R4 | W | R0 | Y | A | R6 |
|---|---|---|---|---|---|---|---|
| 153 | Me | Me | S | H | NHtBu | O | 4-chloro-3-trifluoro-methylphenyl |
| 154 | Me | Me | S | H | NHtBu | O | 4-fluoro-3-trifluoro-methylphenyl |
| 155 | Me | Me | S | H | NHtBu | O | 3-tbutyl-phenyl |
| 156 | Me | Me | S | H | NMe2 | O | 4-chloro-3-trifluoro-methylphenyl |
| 157 | Me | Me | S | H | NMe2 | O | 4-fluoro-3-trifluoro-methylphenyl |
| 158 | Me | Me | S | H | NHEt | O | 4-chloro-3-trifluoro-methylphenyl |
| 159 | Me | Me | S | H | NH2 | O | 3-tbutyl-phenyl |
| 160 | Me | Me | S | H | NH2 | O | 4-chloro-3-trifluoro-methylphenyl |
| 161 | Me | Me | S | H | 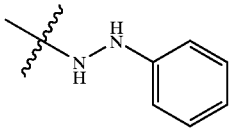 | O | 3-tbutyl-phenyl |
| 162 | Me | Me | S | H | 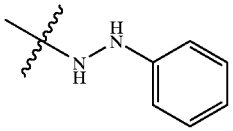 | O | 4-chloro-3-trifluoro-methylphenyl |
| 163 | Me | Me | S | H | 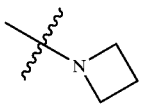 | O | 4-fluoro-3-trifluoro-methylphenyl |
| 164 | Me | Me | S | H | 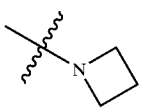 | O | 3-tbutyl-phenyl |
| 165 | Me | Me | S | H | 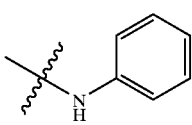 | O | 4-chloro-3-trifluoro-methylphenyl |
| 166 | Me | Me | S | H |  | O | 4-chloro-3-trifluoro-methylphenyl |

TABLE 1-continued

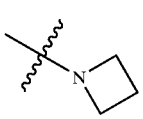

| Compound | R5 | R4 | W | R0 | Y | A | R6 |
|---|---|---|---|---|---|---|---|
| 167 | Me | Me | S | H | 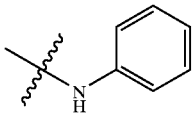 | O | 4-fluoro-3-trifluoro-methylphenyl |
| 168 | Me | Me | S | H | 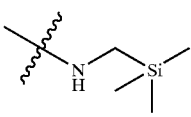 | O | 4-fluoro-3-trifluoro-methylphenyl |
| 169 | Me | Me | S | H | 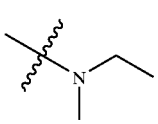 | O | 4-chloro-3-trifluoro-methylphenyl |
| 170 | Me | Me | S | H | 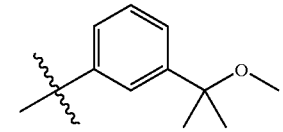 | O |  |
| 171 | Me | Me | S | H | 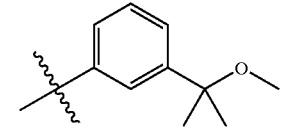 | O |  |

N.B.: Me means methyl, Et means ethyl, Pr means propyl, Bu means butyl, Ph means phenyl, n means linear, i means iso, t means tert.
For reasons of clarity, the indices have not been represented; thus CH2 means $CH_2$, CO2 means $CO_2$, etc.

The analytical characteristics of the compounds of Table 1 are described in the following table.

TABLE 2

| Compound | m.p. (° C.) | NMR (CDCl$_3$) | (M + 1) |
|---|---|---|---|
| 1 | 135 | | |
| 2 | 183 | | |
| 3 | | | 370 |
| 4 | 177 | | |
| 5 | 93 | | |
| 6 | | | 342 |
| 7 | | | 398 |
| 8 | 201 | | |
| 9 | 156 | | |
| 10 | 133 | | |
| 11 | 167 | | |
| 12 | 157 | | |
| 13 | | | 327 |
| 14 | 133 | | |
| 15 | 186 | | |
| 16 | | 1.30 (s, 9H, (CH$_3$)$_3$); 2.05 (s, 3H, ArCH$_3$); 2.30 (s, 3H, ArCH$_3$) | |
| 17 | | 1.30 (s, 9H, (CH$_3$)$_3$); 2.15 (s, 3H, ArCH$_3$); 2.20 (s, 3H, ArCH$_3$); 3.35 (s, 3H, OCH$_3$); 4.05 (m, 2H, CH$_2$NH); 5.30 (bs, 1H, NH); 5.45 (t, 1H, NCH(OCH$_3$)CH$_2$) | |
| 18 | 125 | | |
| 19 | 104 | | |
| 20 | 146 | | |
| 21 | 147 | | |
| 22 | 108 | | |
| 23 | 131 | | |
| 24 | 136 | | |
| 25 | 174 | | |
| 26 | 139 | | |

TABLE 2-continued

| Compound | m.p. (° C.) | NMR (CDCl₃) | (M + 1) |
|---|---|---|---|
| 27 | 125 | | |
| 28 | 70 | | |
| 29 | 123 | | |
| 30 | 141 | | |
| 31 | 131 | | |
| 32 | 182 | | |
| 33 | 96 | | |
| 34 | 115 | | |
| 35 | 96 | | |
| 36 | | 1.15 (s, 9H, ArC(CH₃)₃); 2.15 (s, 3H, Ar(CH₃)); 2.20 (s, 3H, Ar(CH₃)) | |
| 37 | | 2.17 (s, 3H, ArCH₃); 2.20 (s, 3H, ArCH₃); 3.13 (s, 6H, N(CH₃)₂) | |
| 38 | | 1.10 (d, 6H, CH(CH₃)₂); 1.30 (s, 9H, (CH₃)₃); 2.15 (s, 3H, ArCH₃); 2.20 (s, 3H, ArCH₃); 4.00 (m, 1H, CH(CH₃)₂); 4.45 (d, 1H, CONH); 5.95 (s, 1H, ArNH) | |
| 39 | | | 384 |
| 40 | 147 | | |
| 41 | 88 | | |
| 42 | 191 | | |
| 43 | 122 | | |
| 44 | | 1.30 (s, 9H, (CH₃)₃); 2.05 (s, 3H, ArCH₃); 2.25 (s, 3H, ArCH₃); 3.40 (s, 3H, NCH₃); 4.25 (s, 2H, COCH₂N) | |
| 45 | | 1.30 (s, 9H, (CH₃)₃); 1.95 (s, 3H, ArCH₃); 2.15 (s, 3H, ArCH₃); 4.20 (s, 2H, COCH₂S) | |
| 46 | | 1.30 (s, 9H, (CH₃)₃); 1.80 (t, 3H, COCH(CH₃)S); 1.95 (s, 3H, ArCH₃); 2.30 (s, 3H, ArCH₃); 4.40 (m, 1H, COCH(CH₃)S) | |
| 47 | 63 | | |
| 48 | 134 | | |
| 49 | 89 | | |
| 50 | 136 | | |
| 51 | 164 | | |
| 52 | 122 | | |
| 53 | | 1.25 (s, 9H, C(CH₃)₃); 2.15 (s, 3H, ArCH₃); 2.20 (s, 3H, ArCH₃) | |
| 54 | | 1.20 (t, 3H, CH₂CH₃); 1.25 (s, 9H, C(CH₃)₃); 2.15 (s, 3H, ArCH₃); 2.20 (s, 3H, ArCH₃); 2.75 (s, 3H, NCH₃); 3.90 (m, 2H, NCH₂); 4.3 (m, 4H, NCH₂N) | |
| 55 | | 1.15 (m, 6H, 2CH₂CH₃); 1.20 (s, 9H, C(CH₃)₃); 2.15 (s, 3H, ArCH₃); 2.20 (s, 3H, ArCH₃); 2.95 (m, 2H, CH₂CH₃); 3.9 (m, 2H, NCH₂CH₃); 4.4 (m, 4H, 2NCH₂N) | |
| 56 | | 1.1 (t, 3H, CH₂CH₃); 1.25 (s, 9H, C(CH₃)₃); 2.10 (s, 3H, ArCH₃); 2.20 (s, 3H, ArCH₃); 3.8 (q, 2H, NCH₂) | |
| 57 | | | 401 |
| 58 | | | 417 |
| 59 | | | 711 |
| 60 | | | 383 |
| 61 | | | 355 |
| 62 | | | 427 |
| 63 | | | 381 |
| 64 | | | 405 |
| 65 | | 3.44 (q, 2H, NCH₂); 3.03 (s, 3H, NCH₃); 2.19 (s, 3H, ArCH₃); 2.12 (s, 3H, ArCH₃); 1.22 (t, 3H, NCH₂CH₃) | |
| 66 | | 3.88 (s, 2H, NNH₂); 3.24 (s, 3H, NCH₃); 2.19 (s, 3H, ArCH₃); 2.12 (s, 3H, ArCH₃) | |
| 67 | | 8.25 (s, 2H, CONH₂); 2.22 (s, 6H, ArCH₃); 2.07 (s, 6H, ArCH₃) | |
| 68 | | 2.05 (s, 3H, ArCH₃); 2.16 (s, 3H, ArCH₃) | |
| 69 | | 2.79 (M, 4H, NCH₂); 2.17 (s, 3H, ArCH₃); 2.05 (s, 3H, ArCH₃) | |
| 70 | | 2.10 (s, 3H, ArCH₃); 2.04 (s, 3H, ArCH₃) | |
| 71 | | 2.14 (s, 3H, ArCH₃); 2.05 (s, 3H, ArCH₃) | |
| 72 | | 2.07 (s, 3H, ArCH₃); 2.03 (s, 3H, ArCH₃) | |
| 73 | | 2.16 (s, 3H, ArCH₃); 2.05 (s, 3H, ArCH₃) | |
| 74 | | 3.60 (s, 3H, OCH₃); 2.14 (s, 3H, ArCH₃); 2.05 (s, 3H, ArCH₃) | |
| 75 | | 2.14 (s, 3H, ArCH₃); 2.05 (s, 3H, ArCH₃) | |
| 76 | | 2.14 (s, 3H, ArCH₃); 2.05 (s, 3H, ArCH₃); 1.86 (s, 3H, COCH₃) | |
| 77 | | 2.15 (s, 3H, ArCH₃); 2.07 (s, 3H, ArCH₃) | |
| 78 | | 2.17 (s, 3H, ArCH₃); 2.07 (s, 3H, ArCH₃) | |
| 79 | | 3.04 (m, 4H, NCH₂); 2.22 (s, 3H, ArCH₃); 2.17 (s, 3H, ArCH₃) | |
| 80 | | 2.22 (s, 3H, ArCH₃); 2.15 (s, 3H, ArCH₃); 1.21 (d, 6H, NCH(CH₃)) | |
| 81 | | 2.13 (s, 3H, ArCH₃); 2.07 (s, 3H, ArCH₃) | |
| 82 | | 2.06 (s, 3H, ArCH₃); 2.05 (s, 3H, ArCH₃) | |
| 83 | | 2.16 (s, 3H, ArCH₃); 2.07 (s, 3H, ArCH₃) | |
| 84 | | 2.60 (s, 3H, OCH₃); 2.13 (s, 3H, ArCH₃); 2.07 (s, 3H, ArCH₃) | |
| 85 | | 2.16 (s, 3H, ArCH₃); 2.07 (s, 3H, ArCH₃) | |
| 86 | | 2.13 (s, 3H, ArCH₃); 2.06 (s, 3H, ArCH₃); 1.86 (s, 3H, COCH₃) | |
| 87 | | 2.64 (s, 6H, NCH₃); 2.21 (s, 3H, ArCH₃); 2.16 (s, 3H, ArCH₃) | |
| 88 | | 3.24 (s, 3H, NCH₃); 2.19 (s, 3H, ArCH₃); 2.13 (s, 3H, ArCH₃) | |
| 89 | | 3.11 (q, 2H, NCH₂CH₃); 2.14 (s, 3H, ArCH₃); 2.04 (s, 3H, ArCH₃); 1.07 (t, 3H, NCH₂CH₃) | |
| 90 | | 3.75 (m, 1H, NCH(CH₃)₂); 2.13 (s, 3H, ArCH₃); 2.04 (s, 3H, ArCH₃); 1.11 (d, 6H, NCH(CH₃)₂) | |
| 91 | | 2.55 (m, 1H, NHCH(CH₂)₂); 2.14 (s, 3H, ArCH₃); 2.05 (s, 3H, ArCH₃); 0.65 (m, 2H, NCH(CH₂)₂); 0.42 (m, 2H, NCH(CH₂)₂) | |
| 92 | | 3.42 (m, 4H, NCH₂); 2.13 (s, 3H, ArCH₃); 2.07 (s, 3H, ArCH₃) | |
| 93 | | 3.40 (t, 2H, OCH₂); 3.30 (s, 3H, OCH₃); 3.27 (t, 2H, NCH₂); 2.14 (s, 3H, ArCH₃); 2.04 (s, 3H, ArCH₃) | |
| 94 | | 2.22 (s, 3H, ArCH₃); 2.08 (s, 3H, ArCH₃) | |
| 95 | | 4.45 (d, 2H, NHCH₂Ph); 2.16 (s, 3H, ArCH₃); 2.05 (s, 3H, ArCH₃) | |
| 96 | | 4.82 (q, 1H, NCH); 2.15 (s, 3H, ArCH₃); 2.02 (s, 3H, ArCH₃); 1.40 (d, 3H, NCH(CH₃)) | |
| 97 | | 3.93 (t, 4H, NCH₂); 2.15 (s, 3H, ArCH₃); 2.0 (s, 3H, ArCH₃) | |
| 98 | | 3.62 (m, 4H, NCH₂); 3.42 (m, 4H, CH₂O); 2.13 (s, 3H, ArCH₃); 2.07 (s, 3H, ArCH₃) | |
| 99 | | 2.29 (s, 3H, ArCH₃); 2.10 (s, 3H, ArCH₃) | |
| 100 | | 2.23 (s, 3H, ArCH₃); 2.08 (s, 3H, ArCH₃) | |
| 101 | | 3.89 (s, 3H, OCH₃); 2.22 (s, 3H, ArCH₃); 2.08 (s, 3H, ArCH₃) | |
| 102 | | 2.22 (s, 3H, ArCH₃); 2.09 (s, 3H, ArCH₃) | |
| 103 | | 9.36 (s, 1H, CCHN); 2.22 (s, 3H, ArCH₃); 2.09 (s, 3H, ArCH₃) | |
| 104 | | 3.95 (m, 2H, CH₂CF₃); 2.14 (s, 3H, ArCH₃); 2.04 (s, 3H, ArCH₃) | |

TABLE 2-continued

| Compound | m.p. (° C.) | NMR (CDCl₃) | (M + 1) |
|---|---|---|---|
| 105 | | 2.92 (s, 3H, NCH₃); 2.09 (s, 3H, ArCH₃); 2.04 (s, 3H, ArCH₃); 1.34 (s, 9H, NCCH₃) | |
| 106 | | 2.32 (s, 3H, ArCH₃); 2.11 (s, 3H, ArCH₃) | |
| 107 | | 3.67 (s, 3H, OCH₃); 2.16 (s, 3H, ArCH₃); 2.08 (s, 3H, ArCH₃) | |
| 108 | | 4.12 (q, 2H, OCH₂); 2.16 (s, 3H, ArCH₃); 2.08 (s, 3H, ArCH₃); 1.25 (t, 3H, OCH₂CH₃) | |
| 109 | | 4.87 (m, 1H, OCH); 2.15 (s, 3H, ArCH₃); 2.08 (s, 3H, ArCH₃); 1.26 (t, 6H, OCH(CH₃)₃) | |
| 110 | | 5.14 (s, 2H, OCH₂Ph); 2.14 (s, 3H, ArCH₃); 2.06 (s, 3H, ArCH₃) | |
| 111 | | | 389 |
| 112 | | | 465 |
| 113 | | | 403 |
| 114 | | | 415 |
| 115 | | | 431 |
| 116 | | 3.40 (q, 2H, ArNCH₂); 3.04 (q, 2H, CONCH₂); 2.46 (s, 3H, NCH₃); 2.13 (s, 3H, ArCH₃); 2.08 (s, 3H, ArCH₃); 1.05 (t, 3H, ArNCH₂CH₃); 0.77 (t, 3H, CONCH₂CH₃ | 429 |
| 117 | | 4.56 (s, 2H, ArCH₂N); 3.06 (q, 2H, NCH₂); 2.49 (s, 3H, NCH₃); 1.99 (s, 3H, ArCH₃); 1.93 (s, 3H, ArCH₃); 0.73 (t, 3H, NCH₂CH₃) | |
| 118 | | 3.05 (q, 2H, NCH₂CH₃); 2.90 (s, 3H, ArNCH₃); 2.46 (s, 3H, EtNCH₃); 2.13 (s, 3H, ArCH₃); 2.06 (s, 3H, ArCH₃); 0.76 (t, 3H, NCH₂CH₃) | |
| 119 | | 4.18 (s, 2H, CH₂N); 3.02 (q, 2H, NCH₂); 2.50 (s, 3H, NCH₃); 2.19 (s, 3H, ArCH₃); 2.11 (s, 3H, ArCH₃); 1.00 (t, 3H, NCH₂CH₃) | |
| 120 | | 3.94 (d, 2H, CH₂CHCH₂); 3.04 (q, 2H, NCH₂CH₃); 2.47 (s, 3H, NCH₃); 2.10 (s, 3H, ArCH₃); 2.05 (s, 3H, ArCH₃); 0.76 (t, 3H, NCH₂CH₃) | |
| 121 | | 5.30 (q, 1H, NCH); 4.03 (q, 2H, NCH₂CH₃); 2.47 (s, 3H, NCH₃); 2.01 (s, 3H, ArCH₃); 1.82 (s, 3H, ArCH₃); 1.40 (d, 3H, NCH₂CH₃); 0.63 (t, 3H, NCH₂CH₃) | |
| 122 | | | 373 |
| 123 | | 4.83 (m, 3H, NCH₃S); 3.97 (m, 2H, NCH₂); 3.18 (m, 2H, SCH₂); 2.22 (s, 3H, ArCH₃); 2.17 (s, 3H, ArCH₃); 1.31 (s, 9H, C(CH₃)₃) | |
| 124 | | 5.37 (m, 1H, NCH); 3.00 (s, 3H, NCH₃); 2.09 (s, 3H, ArCH₃); 2.06 (s, 3H, ArCH₃); 1.11 (d, 6H, NCH(CH₃)₂) | |
| 125 | | | 386 |
| 126 | | 4.74 (d, 2H, NCH₂Ph); 2.07 (s, 3H, ArCH₃); 1.80 (s, 3H, ArCH₃); 1.25 (s, 9H, CCH₃) | |
| 127 | | | 384 |
| 128 | | | 388 |
| 129 | | | 436 |
| 130 | | | 413 |
| 131 | | | 444 |
| 132 | | | 446 |
| 133 | | | 432 |
| 134 | | | 466 |
| 135 | | | 430 |
| 136 | | | 416 |
| 137 | | | 459 |
| 138 | | | 434 |
| 139 | | | 482 |
| 140 | | | 427 |
| 141 | | | 429 |
| 142 | | | 415 |
| 143 | | | 449 |
| 144 | | | 413 |
| 145 | | | 399 |
| 146 | | | 442 |
| 147 | | | 401 |
| 148 | | | 417 |
| 149 | | | 401 |
| 150 | | | 465 |
| 151 | | | 464 |
| 152 | | | 401 |
| 153 | | | 432 |
| 154 | | | 415 |
| 155 | | | 386 |
| 156 | | | 404 |
| 157 | | | 387 |
| 158 | | | 404 |
| 159 | | | 329 |
| 160 | | | 376 |
| 161 | | | 421 |
| 162 | | | 467 |
| 163 | | | 450 |
| 164 | | | 370 |
| 165 | | | 416 |
| 166 | | | 452 |
| 167 | | 4.05 (t, 4H, NCH₂); 2.07 (s, 3H, ArCH₃); 1.80 (s, 3H, ArCH₃) | |
| 168 | | 2.07 (s, 3H, ArCH₃); 1.80 (s, 3H, ArCH₃) | |
| 169 | | | 461 |
| 170 | | | 387 |
| 171 | | | 360 |

NB: The column (M + 1) represents the (molecular peak + 1) as determined experimentally by the technique of API + mass spectrometry.

Test Examples

The compounds were evaluated for their activity against one or more of the following fungal diseases:

*Phytophthora infestans:* tomato mildew
*Erysiphe graminis f. sp. Tritici:* powdery mildew of wheat
*Pyricularia oryzae:* rice blast
*Leptosphaeria nodorum:* septoria disease of wheat, nodorum variety
*Mycosphaerella graminicola:* septoria disease of wheat, tritici variety
*Puccinia recondita:* brown rust of cereals
*Pyrenophora teres:* net blotch of barley Aqueous solutions or dispersions of the compounds at the desired concentration, including one or more wetting agents, are applied by spraying or by dipping the base of the stem of the test plants, depending on the case. After a given time, the plants or plant parts are inoculated with the appropriate test pathogens, and stored under suitable controlled environmental conditions to maintain the growth of the plant and the development of the disease. After a suitable period, the degree of infection of the infected part of the plant is estimated visually. At a concentration of 500 ppm (weight/volume) or less, the following compounds show, against the specified fungal diseases, control of at least 65% efficacy relative to an untreated control.

*Phytophthora infestans*
44, 45
*Erysiphe graminis f. sp. Tritici*
1, 17, 18, 19, 20, 21, 22, 23, 24, 27, 28, 33, 42, 43, 45, 52, 53, 54, 55, 83, 84, 124, 170
*Pyricularia oryzae*
35
*Leptosphaeria nodorum*
18, 27, 45, 124, 169, 170, 171

*Puccinia recondita*
124, 127, 131, 140, 149, 157, 167, 169, 170
*Pyrenophora teres*
77, 93, 95, 113, 118, 119, 124, 128, 132, 140, 144, 145, 149, 150, 157, 164, 165

What is claimed is:

1. Compound of general formula (I) and salt thereof:

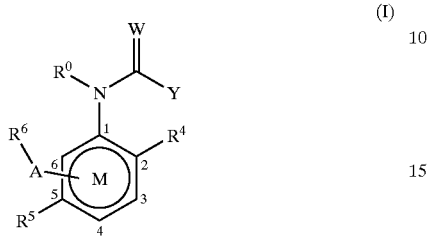

in which
W represents O or S;
Y represents a radical —NR$^1$R$^2$, —OR$^3$ and —SR$^3$;
R$^0$ represents an alkyl, which may be substituted with alkoxy or a hydrogen atom;
R$^1$ and R$^2$, which may be identical or different, represent an alkyl or acyl radical each of which may be substituted with alkoxy; or a hydrogen atom; or —NR$^a$R$^b$, OR$^a$ in which R$^a$ and R$^b$, which may be identical or different, represent an alkyl, acyl or carbocyclyl radical, each of which may be substituted;
R$^3$ represents an alkyl or acyl radical each of which may be substituted with alkoxy; or a hydrogen atom;
R$^1$ and R$^2$ or R$^1$ and R$^0$ or R$^3$ and R$^0$ or R$^a$ and R$^b$, taken together with the atoms connection them, may form an optionally substituted cycle, the assembly thus forming a carbocyclyl or heterocyclyl group;
R$^4$ represents an alkyl radical which may be substituted with halogen atom;
R$^5$ represents an alkyl or acyl radical each of which may be substituted with alkoxy;
R$^6$ represents a phenyl or aromatic heterocyclyl radical;
A represents O or S.

2. The compound of claim 1 wherein R$^5$ is alkyl and A is —O—.

3. Compound according to claim 1, in which:
R$^0$ represents an alkyl, acyl or cyano radical, each of which may be substituted with alkoxy, haolalkoxy, alkylthio, halogen atoms or phenyl optionally substituted with alkyl, haloalkyl, alkoxy, haloalkoxy, alkylthio or halogen atoms; or represents a hydrogen atom;
R$^4$ represents an alkyl, alkenyl, alkynyl, alkoxy, or alkylthio radical, each of which may be substituted with alkoxy, haloalkoxy, alkylthio, halogen atoms or phenyl optionally substituted with alkyl, haloalkyl, alkoxy, haloalkoxy, alkylthio or halogen atoms; or represents hydroxyl; halogen atoms; cyano; acyl;
m represents 0 or 1;
R$^5$ is absent or represents a group defined for R$^4$;
A represents a direct bond, or the divalent radicals —O—, —S—, —NR$^9$—, —CHR$^7$— or —O—CHR$^7$—,
in which R$^9$ represents alkyl, alkenyl or alkynyl, each of which may be substituted with alkoxy, haloalkoxy, alkylthio, halogen atoms or phenyl optionally substituted with alkyl, haloalkyl, alkoxy, haloalkoxy, alkylthio or halogen atoms; or represents a hydrogen atom;
and R$^7$ represents a group defined for R$^9$ according to this characteristic or represents hydroxyl, halogen atoms, cyano, acyl, alkoxy, haolalkoxy, or alkylthio; and
R$^6$ represents a phenyl or aromatic heterocyclyl radical, optionally substituted with one or more substituents, which may be identical or different, and are chosen from hydroxyl, halogen atoms, cyano, acyl (preferably —C(=O)R$^c$, —C(=S)R$^c$ or —S(O)$_p$R$^c$, in which p represents 0, 1 or 2 and R$^c$ represents alkyl, haloalkyl, alkoxy, haloalkoxy, alkylthio, amino, monoalkylamino, dialkylamino or phenyl optionally substituted with alklyl, haloalkyl, alkoxy, haloalkoxy or alkylthio; or phenyloxy, phenylthio, carbocyclyl or heterocyclyl), amino, alkylamino, dialkylamino, alkyl, alkenyl, alkynyl, haloalkyl, R$^a$O—-alkyl, acyloxyalkyl, cyanooxyalkyl, alkoxy, haloalkoxy, alkylthio, carboxyclyl, with alkyl, haloalkyl, alkoxy, haloalkoxy or alkylthio; and benzyl optionally substituted with alkyl, haloalkyl, alkoxy, haloalkoxy or alkylthio.

4. Compound according to claim 3, in which:
the R$^4$ acyl is —C(=O)R$^c$, —C(=S)R$^c$ or —S(O)$_p$R$^c$, in which p represents 0, 1 or 2 and R$^c$ represents alkyl, haloalkyl, alkoxy, haloalkoxy, alkylthio, amino, monoalkyamino, dialkylamino or phenyl optionally substituted with alkyl, haolalkyl, alkoxy, haloalkoxy or alkylthio; or phenyloxy, phenylthio, carbocyclyl or heterocyclyl;
the optionally substituted R$^6$ aromatic heterocyclyl radical is thiazolyl, isothiazolyl, thiadiazolyl, pyridyl or pyrimidinyl, and the optionally substituted R$^6$ carbocyclyl is cyclohexyl or cyclopentyl.

5. Compound according to claim 4, which have at least one of the following characteristics:
R$^4$ represents a C$_1$–C$_{10}$alkyl radical or a halogen atom;
m represents 1;
R$^5$ represents a C$_1$–C$_{10}$alkyl radical or a halogen atom;
A represents a direct bond or a divalent radical —O—, and occupies position 4 on the benzene nucleus M;
R$^6$ represents a phenyl radical optionally substituted with one or more substituents which may be halogens, alkyl, alkenyl, alkynyl, haloalkyl, alkoxyalkyl, hydroxyalkyl, haloalkoxyalkyl, alkoxy, alkylthio, acyl or cyano.

6. Compound according to claim 5, in which R$^5$ occupies position 5 on the nucleus M.

7. Compound according to claim 1, in which:
the R$^4$ acyl is —C(=O)R$^c$, —C(=S)R$^c$ or —S(O)$_p$R$^c$, in which p represents 0, 1 or 2 and R$^c$ represents alkyl, haloalkyl, alkoxy, haloalkoxy, alkylthio, amino, monoalkylamino, dialkylamino or phenyl optionally substituted with alkyl, haolalkyl, alkoxy, haloalkoxy or alkylthio; or phenyloxy, phenylthio, carbocyclyl or heterocyclyl;
the optionally substituted R$^6$ aromatic heterocyclyl radical is thiazolyl, isothiazolyl, thiadiazolyl, pyridyl or pyrimidinyl, and the optionally substituted R$^6$ carbocyclyl is cyclohexyl or cyclopentyl.

8. Compound according to claim 7, which have at least one of the following characteristics:
R$^4$ represents a C$_1$–C$_{10}$alkyl radical or a halogen atom;
m represents 1;
R$^5$ represents a C$_1$–C$_{10}$alkyl radical or a halogen atom;
A represents a direct bond or a divalent radical —O—, and occupies position 4 on the benzene nucleus M;
R$^6$ represents a phenyl radical optionally substituted with one or more substituents which may be halogens, alkyl, alkenyl, alkynyl, haloalkyl, alkoxyalkyl, hydroxyalkyl, haloalkoxyalkyl, alkoxy, alkylthio, acyl or cyano.

9. Compound according to claim 8, in which $R^5$ occupies position 5 on the nucleus M.

10. Fungicidal composition comprising at least one compound according to claim 1, or a salt thereof, mixed with an agriculturally acceptable diluent or suppport.

11. Fungicidal composition comprising at least one compound according to claim 3, or a salt thereof, mixed with an agriculturally acceptable diluent or support.

12. Fungicidal composition comprising at least one compound according to claim 4, or a salt thereof, mixed with an agriculturally acceptable diluent or support.

13. Fungicidal composition comprising at least one compound according to claim 5, or a salt thereof, mixed with an agriculturally acceptable diluent or support.

14. Fungicidal composition comprising at least one compound according to claim 6, or a salt thereof, mixed with an agriculturally acceptable diluent or support.

15. Method for combating phytopathogenic fungi at a site which is infested or liable to be infested with them, which comprises the application at this site of a compound according to claim 1 a salt thereof.

16. Method for combating phytopathogenic fungi at a site which is infested or liable to be infested with them, which comprises the application at this site of a compound according to claim 3 or a salt thereof.

17. Method for combating phytopathogenic fungi at a site which is infested or liable to be infested with them, which comprises the application at this site of a compound according to claim 4 or a salt thereof.

18. Method for combating phytopathogenic fungi at a site which is infested of liable to be infested with them, which comprises the application at this site of a compound according to claim 5 or a salt thereof.

19. Method for combating phytopathogenic fungi at a site which is infested or liable to be infested with them, which comprises the application at this site of a compound according to claim 6 or a salt thereof.

* * * * *

UNITED STATES PATENT AND TRADEMARK OFFICE
CERTIFICATE OF CORRECTION

PATENT NO.      : 6,696,487 B2  
DATED           : February 24, 2004  
INVENTOR(S)     : Vincent Gerusz et al.

It is certified that error appears in the above-identified patent and that said Letters Patent is hereby corrected as shown below:

<u>Title page,</u>
Item [75], Inventors, should read:
-- [75] Inventors: Vincent Gerusz, San Antonio, Texas (US)
                      Darren James Mansfield, Lyon (FR)
                      José Perez, Lyon (FR)
                      David Tickle, Slough, Berkshire (GB)
                      Jean-Pierre Vors, Lyon (FR)
                      Derek Baldwin, Essex (GB)
                      Thomas Lawley Hough, Cambridge (GB)
                      Dale Robert Mitchell, Essex (GB) --

Signed and Sealed this

Twenty-fifth Day of May, 2004

JON W. DUDAS
*Acting Director of the United States Patent and Trademark Office*